(12) United States Patent
Chester et al.

(10) Patent No.: US 11,639,374 B2
(45) Date of Patent: May 2, 2023

(54) **T CELL RECEPTORS SPECIFIC FOR THE NY-ESO-1 TUMOR ANTIGEN-HLA-A*02 COMPLEX**

(71) Applicant: IMMUNOCORE LIMITED, Abingdon (GB)

(72) Inventors: Fiona Chester, Abingdon (GB); Andrew Alexander Knox, Abingdon (GB); Jonathan Patrick Lowther, Abingdon (GB); Viren Vinubhai Patel, Abingdon (GB); Emma Elizabeth Baston, Abingdon (GB); Ruth Martinez Hague, Abingdon (GB)

(73) Assignee: IMMUNOCORE LIMITED, Abingdon (GB)

( * ) Notice: Subject to any disclaimer, the term of this patent is extended or adjusted under 35 U.S.C. 154(b) by 779 days.

(21) Appl. No.: 16/065,047

(22) PCT Filed: Dec. 22, 2016

(86) PCT No.: PCT/GB2016/054032
§ 371 (c)(1),
(2) Date: Jun. 21, 2018

(87) PCT Pub. No.: WO2017/109496
PCT Pub. Date: Jun. 29, 2017

(65) Prior Publication Data
US 2019/0002523 A1 Jan. 3, 2019

(30) Foreign Application Priority Data

Dec. 22, 2015 (GB) .................................. 1522592

(51) Int. Cl.
| C07K 14/725 | (2006.01) |
| C07K 14/47 | (2006.01) |
| A61K 9/00 | (2006.01) |
| A61K 35/17 | (2015.01) |
| A61K 38/17 | (2006.01) |
| A61K 39/395 | (2006.01) |
| A61K 45/06 | (2006.01) |
| C07K 16/28 | (2006.01) |
| C12N 5/0783 | (2010.01) |
| A61K 39/00 | (2006.01) |
| A61P 35/00 | (2006.01) |

(52) U.S. Cl.
CPC ........ *C07K 14/7051* (2013.01); *A61K 9/0019* (2013.01); *A61K 35/17* (2013.01); *A61K 38/1774* (2013.01); *A61K 39/001188* (2018.08); *A61K 39/3955* (2013.01); *A61K 45/06* (2013.01); *A61P 35/00* (2018.01); *C07K 14/4748* (2013.01); *C07K 16/2809* (2013.01); *C12N 5/0638* (2013.01); *A61K 2039/5156* (2013.01); *A61K 2039/54* (2013.01); *A61K 2039/545* (2013.01); *A61K 2039/605* (2013.01); *C07K 2319/30* (2013.01)

(58) Field of Classification Search
None
See application file for complete search history.

(56) References Cited

FOREIGN PATENT DOCUMENTS

| CN | 1989153 A | 6/2007 |
| WO | WO 2001/62908 A2 | 8/2001 |
| WO | WO 2003/020763 A3 | 5/2003 |
| WO | WO 2004/033685 A1 | 4/2004 |
| WO | WO 2005/113595 A2 | 12/2005 |
| WO | WO 2005/114215 A2 | 12/2005 |
| WO | WO 2008/037943 A1 | 4/2008 |
| WO | WO 2008/039818 A3 | 8/2008 |
| WO | WO 2012/038055 A1 | 3/2012 |
| WO | WO 2014/160030 A2 | 10/2014 |
| WO | WO 2017/109496 A1 | 6/2017 |

OTHER PUBLICATIONS

Wucherpfennig et al (Cold Spring Harbor Perspectives in Biology, 2:a005140, 2009).*
Jefferis, R., "Glycosylation as a strategy to improve antibody-based therapeutics," Nature Reviews Drug Discovery, Mar. 2009, vol. 8, pp. 226-234.
Liddy, N. et al.," Monoclonal TCR-redirected tumor cell killing", nature medicine, May 6, 2012, vol. 18, No. 6, pp. 980-987.
Rosenberg et al., "Adoptive cell transfer: a clinical path to effective cancer immunotherapy," Nature Reviews Cancer, Apr. 2008, 8(4):299-308.
Sinclair, A.M. and Elliott, "Glycoengineering: The effect of glycosylation on the properties of therapeutic proteins," Journal of Pharmaceutical Sciences, vol. 94, Issue 8, Aug. 2005, pp. 1626-1635.
Weidanz et al., "Display of functional αβ single-chain T-cell receptor molecules on the surface of bacteriophage," Journal of Immunological Methods, vol. 221, Issues 1-2, Dec. 1998, pp. 59-76.
Derre, L., et al., "Distinct sets of αβ TCRs confer similar recognition of tumor antigen NY-ESO-1157-165 by interacting with its central Met/Trp residues," PNAS, Sep. 30, 2008, vol. 105, No. 39, 13 pages.
International Search Report and Written Opinion, PCT Application No. PCT/GB2016/054032, dated Mar. 13, 2017, 20 pages.

(Continued)

Primary Examiner — Patricia Duffy
(74) Attorney, Agent, or Firm — Fenwick & West LLP

(57) ABSTRACT

The present invention relates to T cell receptors (TCRs) which bind the HLA-A*02 restricted peptide SLLMWITQC derived from the cancer antigen NY-ESO-1. Said TCRs may comprise mutations within the alpha and/or beta variable domains relative to a native NY-ESO-1 TCR. The TCRs of the invention are particularly suitable for use as novel immunotherapeutic reagents for the treatment of malignant disease.

14 Claims, 15 Drawing Sheets
Specification includes a Sequence Listing.

(56) References Cited

OTHER PUBLICATIONS

Li, Y., et al., Directed evolution of human T-cell receptors with picomolar affinities by phage display, *Nature Biotechnology*, Mar. 2005, vol. 23, No. 3, pp. 349-354.

McCormack, E., et al., "Bi-specific TCR-anti CD3 redirected T-cell targeting of NY-ESO-1-and LAGE-1-positive tumors," *Cancer immunology Immunotherapy*, Dec. 22, 2012, vol. 62, No. 4, pp. 773-785.

Robbins, P.F., et al. "Single and Dual Amino Acid Substitutions in TCR CDR's Can Enhance Antigen-Specific T Cell Functions," *The Journal of Immunology*, May 1, 20018, vol. 180, No. 9, pp. 6116-6131.

Hamidi, M. et al., "Pharmacokinetic Consequences of Pegylation," Drug Delivery, 2006, 13:6, pp. 399-409, DOI: 10.1080/10717540600814402.

Wooldridge, L. et al., "A Single Autoimmune T Cell Receptor Recognizes More Than a Million Different Peptides," *The Journal of Biological Chemistry*, vol. 287, No. 2, 2012, pp. 1168-1177.

Zhao, Y. et al.,"High-Affinity TCRs Generated by Phage Display Provide CD4$^+$ T Cells with the Ability to Recognize and Kill Tumor Cell Lines," *The Journal of Immunology*, The American Association of Immunologists, US, vol. 179, No. 9, Nov. 1, 2007, pp. 5845-5854.

\* cited by examiner

SEQ ID NO: 2 Amino acid sequence of the wild-type alpha chain variable domain. CDRs are underlined and CDR1, 2, 3 are designated SEQ ID NO: 41, 42 and 43, respectively. The constant region is shown in italics. The FM2 and FM3 regions are in bold and are designated SEQ ID NO: 47 and 48, respectively.

AQSVAQPEDQVNVAEGNPLTVKCTYS<u>VSGNPY</u>LFWYVQYPNRGLQFLLK<u>YITGDNLV</u>KGSY GFEAEFNKSQTSFHLKKPSALVSDSALYF<u>CAVRDINSGAGSYQLTF</u>GKGTKLSVIP*NIQNP DPAVYQLRDSKSSDKSVCLFTDFDSQTNVSQSKDSDVYITDKTVLDMRSMDFKSNSAVAWS NKSDFACANAFNNSIIPEDTFFPSPESS*

SEQ ID NO: 3 Amino acid sequence of the wild-type beta chain variable domain. CDRs are underlined and are designated SEQ ID NO: 44, 45 and 46, respectively. The constant region is shown in italics. The FM2 and FM3 regions are in bold and are designated SEQ ID NO: 49 and 50, respectively.

SAVISQKPSRDICQRGTSLTIQCQVDS<u>QVTM</u>MFWYRQQPGQSLTLIAT<u>ANQGSEA</u>TYESGF VIDKFPISRPNLTFSTLTVSNMSPEDSSIYL<u>CSVGGSGGADTQYF</u>GPGTRLTVL*EDLKNVF PPEVAVFEPSEAEISHTQKATLVCLATGFYPDHVELSWWVNGKEVHSGVSTDPQPLKEQPA LNDSRYCLSSRLRVSATFWQNPRNHFRCQVQFYGLSENDEWTQDRAKPVTQIVSAEAWGRA D*

FIG. 1

SEQ ID NO: 4 Amino acid sequence of the soluble extracellular region of a native alpha chain of the invention. CDRs are underlined. The constant region is shown in italics and the non-native cysteine residue is shown in bold (at position 48 of constant region).

AQSVAQPEDQVNVAEGNPLTVKCTYS<u>VSGNPY</u>LFWYVQYPNRGLQFLLK<u>YITGDN</u>LVKGSY GFEAEFNKSQTSFHLKKPSALVSDSALYF<u>CAVRDINSGAGSYQLTF</u>GKGTKLSVIP*NIQNP DPAVYQLRDSKSSDKSVCLFTDFDSQTNVSQSKDSDVYITDKCVLDMRSMDFKSNSAVAWS NKSDFACANAFNNSIIPEDTFFPSPESS*

SEQ ID NO: 5 Amino acid sequence of the soluble extracellular region of a native beta chain of the invention. CDRs are underlined. The constant region is shown in italics and the non-native cysteine residue is shown in bold (at position 57 of constant region). Additional non-native amino acids at position 75 and position 89 of the constant region are also shown in bold.

SAVISQKPSRDICQRGTSLTIQCQVDS<u>QVTM</u>MFWYRQQPGQSLTLIATA<u>NQGSEA</u>TYESGF VIDKFPISRPNLTFSTLTVSNMSPEDSSIYL<u>CSVGGSGGADTQYF</u>GPGTRLTVL*EDLKNVF PPEVAVFEPSEAEISHTQKATLVCLATGFYPDHVELSWWVNGKEVHSGVCTDPQPLKEQPA LNDSRYALSSRLRVSATFWQDPRNHFRCQVQFYGLSENDEWTQDRAKPVTQIVSAEAWGRA D*

FIG. 2

Amino acid sequences of mutated TCR alpha chain variable regions of the invention

SEQ ID NO: 6 mutant alpha chain (a12) CDRs are underlined, mutations in bold

AQSVAQPEDQVNVAEGNPLTVKCTYS<u>VSGNPY</u>LFWYVQYPNRGLQFLLKY<u>ITGDNLVKGSY
GFEAEF</u>NKSQTSFHLKKPSALVSDSALYF<u>CAVRDSDQHAGSYQLTF</u>GKGTKLSVIP

SEQ ID NO: 7 mutant alpha chain (a24) CDRs are underlined, mutations in bold

AQSVAQPEDQVNVAEGNPLTVKCTYS<u>VSGNPY</u>LFWYVQYPNRGLQFLLKY<u>LGDSALVKGSY
GFEAEF</u>NKSQTSFHLKKPSALVSDSALYF<u>CAVRDINSGAGSYQLTF</u>GKGTKLSVIP

SEQ ID NO: 8 mutant alpha chain (a24l) CDRs are underlined, mutations in bold

AQSVAQPEDLVNVAEGNPLTVKCTYS<u>VSGNPY</u>LFWYVQYPNRGLQFLLKY<u>LGDSALVKGSY
GFEAEF</u>NKSQTSFHLKKPSALVSDSALYF<u>CAVRDINSGAGSYQLTF</u>GKGTKLSVIP

SEQ ID NO: 9 mutant alpha chain (a28) CDRs are underlined, mutations in bold

AQSVAQPEDQVNVAEGNPLTVKCTYS<u>VSGNPY</u>LFWYVQYPNRGLQFLLKY<u>ITGDNLVKGSY
GFEAEF</u>NKSQTSFHLKKPSALVSDSALYF<u>CAVRSSRQHAGSYQLTF</u>GKGTKLSVIP

SEQ ID NO: 10 mutant alpha chain (a78l) CDRs are underlined, mutations in bold

AQSVAQPEDLVNVAEGNPLTVKCTYS<u>VSGNPY</u>LFWYVQYPNRGLQFLLKY<u>LGDSALVKGSY
GFEAEF</u>NKSQTSFHLKKPSALVSDSALYF<u>CAVRDIDSGAGSYQLTF</u>GKGTKLSVIP

SEQ ID NO: 11 mutant alpha chain (a82l) CDRs are underlined, mutations in bold

AQSVAQPEDLVNVAEGNPLTVKCTYS<u>VSGNPY</u>LFWYVQYPNRGLQFLLKY<u>LGDSALVKGSY
GFEAEF</u>NKSQTSFHLKKPSALVSDSALYF<u>CAVRDIRSGAGSYQLTF</u>GKGTKLSVIP

SEQ ID NO: 12 mutant alpha chain (a82) CDRs are underlined, mutations in bold

AQSVAQPEDQVNVAEGNPLTVKCTYS<u>VSGNPY</u>LFWYVQYPNRGLQFLLKY<u>LGDSALVKGSY
GFEAEF</u>NKSQTSFHLKKPSALVSDSALYF<u>CAVRDIRSGAGSYQLTF</u>GKGTKLSVIP

SEQ ID NO: 51 mutant alpha chain (a86) CDRs are underlined, mutations in bold

AQSVAQPEDQVNVAEGNPLTVKCTYS<u>VSGNPY</u>LFWYVQYPNRGLQFLLKY<u>LTDDNLVKGSY
GFEAEF</u>NKSQTSFHLKKPSALVSDSALYF<u>CAVRDINSGAGSYQLTF</u>GKGTKLSVIP

FIG. 3

Amino acid sequences of mutated TCR beta chain variable regions of the invention

SEQ ID NO: 13 mutant beta chain (b5) CDRs are underlined, mutations in bold

SAVISQKPSRDIKQRGTSLTIQCQVDSQVTMMFWYRQQPGQSPTLIATAWTGGEATYESGF
VIDKFPISRPNLTFSTLTVSNMSPEDSSIYLCSVGGSGGADTQYFGPGTRLTVL

SEQ ID NO: 14 mutant beta chain (b12) CDRs are underlined, mutations in bold

SAVISQKPSRDIKQRGTSLTIQCQVDKRLALMFWYRQQPGQSPTLIATAWTGGEATYESGF
VIDKFPISRPNLTFSTLTVSNMSPEDSSIYLCSVGGSGGADTQYFGPGTRLTVL

SEQ ID NO: 15 mutant beta chain (b52) CDRs are underlined, mutations in bold

SAVISQKPSRDIKQRGTSLTIQCQVDKRLALMFWYRQQPGQSPTLIATAWTGGEATYESGF
VIDKFPISRPNLTFSTLTVSNMSPEDSSIYLCSVGGSGAADTQYFGPGTRLTVL

SEQ ID NO: 16 mutant beta chain (b56) CDRs are underlined, mutations in bold

SAVISQKPSRDIKQRGTSLTIQCQVDKRLAMFWYRQQPGQSPTLIATAWTGGEATYESGF
VIDKFPISRPNLTFSTLTVSNMSPEDSSIYLCSVGGSGGADTQYFGPGTRLTVL

SEQ ID NO: 17 mutant beta chain (b56l) CDRs are underlined, mutations in bold

SAVISQKPSRDIKQRGTSLTIQCQVDKRLAMFWYRQQPGQSLTLIATAWTGGEATYESGF
VIDKFPISRPNLTFSTLTVSNMSPEDSSIYLCSVGGSGGADTQYFGPGTRLTVL

SEQ ID NO: 18 mutant beta chain (b65) CDRs are underlined, mutations in bold

SAVISQKPSRDIKQRGTSLTIQCQVDKRLALMFWYRQQPGQSPTLIATAWTGSEATYESGF
VIDKFPISRPNLTFSTLTVSNMSPEDSSIYLCSVGGSGGADTQYFGPGTRLTVL

SEQ ID NO: 19 mutant beta chain (b65l) CDRs are underlined, mutations in bold

SAVISQKPSRDIKQRGTSLTIQCQVDKRLALMFWYRQQPGQSLTLIATAWTGSEATYESGF
VIDKFPISRPNLTFSTLTVSNMSPEDSSIYLCSVGGSGGADTQYFGPGTRLTVL

SEQ ID NO: 20 mutant beta chain (b67) CDRs are underlined, mutations in bold

FIG. 4

SAVISQKPSRDIKQRGTSLTIQCQVDKRLAMMFWYRQQPGQSPTLIATAWTGGEATYESGF
VIDKFPISRPNLTFSTLTVSNMSPEDSSIYLCSVGGSGAADTQYFGPGTRLTVL

SEQ ID NO: 21 mutant beta chain (b67l) CDRs are underlined, mutations in bold

SAVISQKPSRDIKQRGTSLTIQCQVDKRLAMMFWYRQQPGQSLTLIATAWTGGEATYESGF
VIDKFPISRPNLTFSTLTVSNMSPEDSSIYLCSVGGSGAADTQYFGPGTRLTVL

SEQ ID NO: 22 mutant beta chain (b68) CDRs are underlined, mutations in bold

SAVISQKPSRDIKQRGTSLTIQCQVDKRLAMMFWYRQQPGQSPTLIATAWTGSEATYESGF
VIDKFPISRPNLTFSTLTVSNMSPEDSSIYLCSVGGSGGADTQYFGPGTRLTVL

SEQ ID NO: 23 mutant beta chain (b68l) CDRs are underlined, mutations in bold

SAVISQKPSRDIKQRGTSLTIQCQVDKRLAMMFWYRQQPGQSLTLIATAWTGSEATYESGF
VIDKFPISRPNLTFSTLTVSNMSPEDSSIYLCSVGGSGGADTQYFGPGTRLTVL

SEQ ID NO: 52 mutant beta chain (b71) CDRs are underlined, mutations in bold

SAVISQKPSRDIKQRGTSLTIQCQVDSQVAMMFWYRQQPGQSPTLIATAWQGSEATYESGF
VIDKFPISRPNLTFSTLTVSNMSPEDSSIYLCSVGGSGAADTQYFGPGTRLTVL

FIG. 4 Cont'd

Amino acid sequences of alpha and beta chains of ImmTAC molecules of the invention ImmTAC1 (S2C)

SEQ ID NO: 32 ImmTAC alpha chain (comprising SEQ ID NO: 7(a24) and the constant domain of SEQ ID NO: 4, truncated by 8 amino acids)

AQSVAQPEDQVNVAEGNPLTVKCTYSVSGNPYLFWYVQYPNRGLQFLLKYLGDSALVKGSY
GFEAEFNKSQTSFHLKKPSALVSDSALYFCAVRDINSGAGSYQLTFGKGTKLSVIPNIQNP
DPAVYQLRDSKSSDKSVCLFTDFDSQTNVSQSKDSDVYITDKCVLDMRSMDFKSNSAVAWS
NKSDFACANAFNNSIIPEDT

SEQ ID NO: 33 ImmTAC beta chain (comprising an anti-CD3 scFv (bold) fused via a linker (italics) to a TCR beta chain comprising SEQ ID NO: 15(b52) and the constant domain of SEQ ID NO: 3)

**AIQMTQSPSSLSASVGDRVTITCRASQDIRNYLNWYQQKPGKAPKLLIYYTSRLESGVPSR
FSGSGSGTDYTLTISSLQPEDFATYYCQQGNTLPWTFGQGTKVEIKGGGGSGGGGSGGGGS
GGGGSGGGSEVQLVESGGGLVQPGGSLRLSCAASGYSFTGYTMNWVRQAPGKGLEWVALIN
PYKGVSTYNQKFKDRFTISVDKSKNTAYLQMNSLRAEDTAVYYCARSGYYGDSDWYFDVWG
QGTLVTVSS*GGGGS*SAVISQKPSRDIKQRGTSLTIQCQVDKRLALMFWYRQQPGQSPTLIA
TAWTGGEATYESGFVIDKFPISRPNLTFSTLTVSNMSPEDSSIYLCSVGGSGAADTQYFGP
GTRLTVLEDLKNVFPPEVAVFEPSEAEISHTQKATLVCLATGFYPDHVELSWWVNGKEVHS
GVCTDPQPLKEQPALNDSRYALSSRLRVSATFWQDPRNHFRCVQFYGLSENDEWTQDRAK
PVTQIVSAEAWGRAD

FIG. 5

Amino acid sequences of alpha and beta chains of ImmTAC molecules of the invention ImmTAC2 (S2E)

SEQ ID NO: 35 ImmTAC alpha chain (comprising SEQ ID NO: 7(a24) and the constant domain of SEQ ID NO: 4, truncated by 8 amino acids)

AQSVAQPEDQVNVAEGNPLTVKCTYSVSGNPYLFWYVQYPNRGLQFLLKYLGDSALVKGSY
GFEAEFNKSQTSFHLKKPSALVSDSALYFCAVRDINSGAGSYQLTFGKGTKLSVIPNIQNP
DPAVYQLRDSKSSDKSVCLFTDFDSQTNVSQSKDSDVYITDKCVLDMRSMDFKSNSAVAWS
NKSDFACANAFNNSIIPEDT

SEQ ID NO: 36 ImmTAC beta chain (comprising an anti-CD3 scFv (bold) fused via a linker (italics) to a TCR beta chain comprising SEQ ID NO: 18(b65) and the constant domain of SEQ ID NO: 5)

**AIQMTQSPSSLSASVGDRVTITCRASQDIRNYLNWYQQKPGKAPKLLIYYTSRLESGVPSR
FSGSGSGTDYTLTISSLQPEDFATYYCQQGNTLPWTFGQGTKVEIK**GGGGSGGGGSGGGGS
GGGGSGGGS**EVQLVESGGGLVQPGGSLRLSCAASGYSFTGYTMNWVRQAPGKGLEWVALIN
PYKGVSTYNQKFKDRFTISVDKSKNTAYLQMNSLRAEDTAVYYCARSGYYGDSDWYFDVWG
QGTLVTVSS***GGGGS*SAVISQKPSRDIKQRGTSLTIQCQVDKRLALMFWYRQQPGQSPTLIA
TAWTGSEATYESGFVIDKFPISRPNLTFSTLTVSNMSPEDSSIYLCSVGGSGGADTQYFGP
GTRLTVLEDLKNVFPPEVAVFEPSEAEISHTQKATLVCLATGFYPDHVELSWWVNGKEVHS
GVCTDPQPLKEQPALNDSRYALSSRLRVSATFWQDPRNHFRCQVQFYGLSENDEWTQDRAK
PVTQIVSAEAWGRAD

FIG. 6

Amino acid sequences of alpha and beta chains of ImmTAC molecules of the invention ImmTAC3 (S2G)

SEQ ID NO: 37 ImmTAC alpha chain (comprising SEQ ID NO: 12(a82) and the constant domain of SEQ ID NO: 4, truncated by 8 amino acids)

AQSVAQPEDQVNVAEGNPLTVKCTYSVSGNPYLFWYVQYPNRGLQFLLKYLGDSALVKGSY
GFEAEFNKSQTSFHLKKPSALVSDSALYFCAVRDIRSGAGSYQLTFGKGTKLSVIPNIQNP
DPAVYQLRDSKSSDKSVCLFTDFDSQTNVSQSKDSDVYITDKCVLDMRSMDFKSNSAVAWS
NKSDFACANAFNNSIIPEDT

SEQ ID NO: 38 ImmTAC beta chain (comprising an anti-CD3 scFv (bold) fused via a linker (italics) to a TCR beta chain comprising SEQ ID NO: 15(b52) and the constant domain of SEQ ID NO: 5)

**AIQMTQSPSSLSASVGDRVTITCRASQDIRNYLNWYQQKPGKAPKLLIYYTSRLESGVPSR
FSGSGSGTDYTLTISSLQPEDFATYYCQQGNTLPWTFGQGTKVEIKGGGGSGGGGSGGGGS
GGGGSGGGSEVQLVESGGGLVQPGGSLRLSCAASGYSFTGYTMNWVRQAPGKGLEWVALIN
PYKGVSTYNQKFKDRFTISVDKSKNTAYLQMNSLRAEDTAVYYCARSGYYGDSDWYFDVWG
QGTLVTVSS** *GGGGS* SAVISQKPSRDIKQRGTSLTIQCQVDKRLALMFWYRQQPGQSPTLIA
TAWTGGEATYESGFVIDKFPISRPNLTFSTLTVSNMSPEDSSIYLCSVGGSGAADTQYFGP
GTRLTVLEDLKNVFPPEVAVFEPSEAEISHTQKATLVCLATGFYPDHVELSWWVNGKEVHS
GVCTDPQPLKEQPALNDSRYALSSRLRVSATFWQDPRNHFRCVQFYGLSENDEWTQDRAK
PVTQIVSAEAWGRAD

FIG. 7

Amino acid sequences of alpha and beta chains of ImmTAC molecules of the invention ImmTAC4 (S2I)

SEQ ID NO: 39 ImmTAC alpha chain (comprising SEQ ID NO: 12(a82) and the constant domain of SEQ ID NO: 4, truncated by 8 amino acids)

AQSVAQPEDQVNVAEGNPLTVKCTYSVSGNPYLFWYVQYPNRGLQFLLKYLGDSALVKGSY
GFEAEFNKSQTSFHLKKPSALVSDSALYFCAVRDIRSGAGSYQLTFGKGTKLSVIPNIQNP
DPAVYQLRDSKSSDKSVCLFTDFDSQTNVSQSKDSDVYITDKCVLDMRSMDFKSNSAVAWS
NKSDFACANAFNNSIIPEDT

SEQ ID NO: 40 ImmTAC beta chain (comprising an anti-CD3 scFv (bold) fused via a linker (italics) to a TCR beta chain comprising SEQ ID NO: 18(b65) and the constant domain of SEQ ID NO: 5)

**AIQMTQSPSSLSASVGDRVTITCRASQDIRNYLNWYQQKPGKAPKLLIYYTSRLESGVPSR
FSGSGSGTDYTLTISSLQPEDFATYYCQQGNTLPWTFGQGTKVEIK**GGGGSGGGGSGGGGS
GGGGSGGGS**EVQLVESGGGLVQPGGSLRLSCAASGYSFTGYTMNWVRQAPGKGLEWVALIN
PYKGVSTYNQKFKDRFTISVDKSKNTAYLQMNSLRAEDTAVYYCARSGYYGDSDWYFDVWG
QGTLVTVSS**_GGGGS_SAVISQKPSRDIKQRGTSLTIQCQVDKRLALMFWYRQQPGQSPTLIA
TAWTGSEATYESGFVIDKFPISRPNLTFSTLTVSNMSPEDSSIYLCSVGGSGGADTQYFGP
GTRLTVLEDLKNVFPPEVAVFEPSEAEISHTQKATLVCLATGFYPDHVELSWWVNGKEVHS
GVCTDPQPLKEQPALNDSRYALSSRLRVSATFWQDPRNHFRCQVQFYGLSENDEWTQDRAK
PVTQIVSAEAWGRAD

FIG. 8

Further specificity testing of ImmTAC molecules of the invention (Exp. No. PCA002/3)
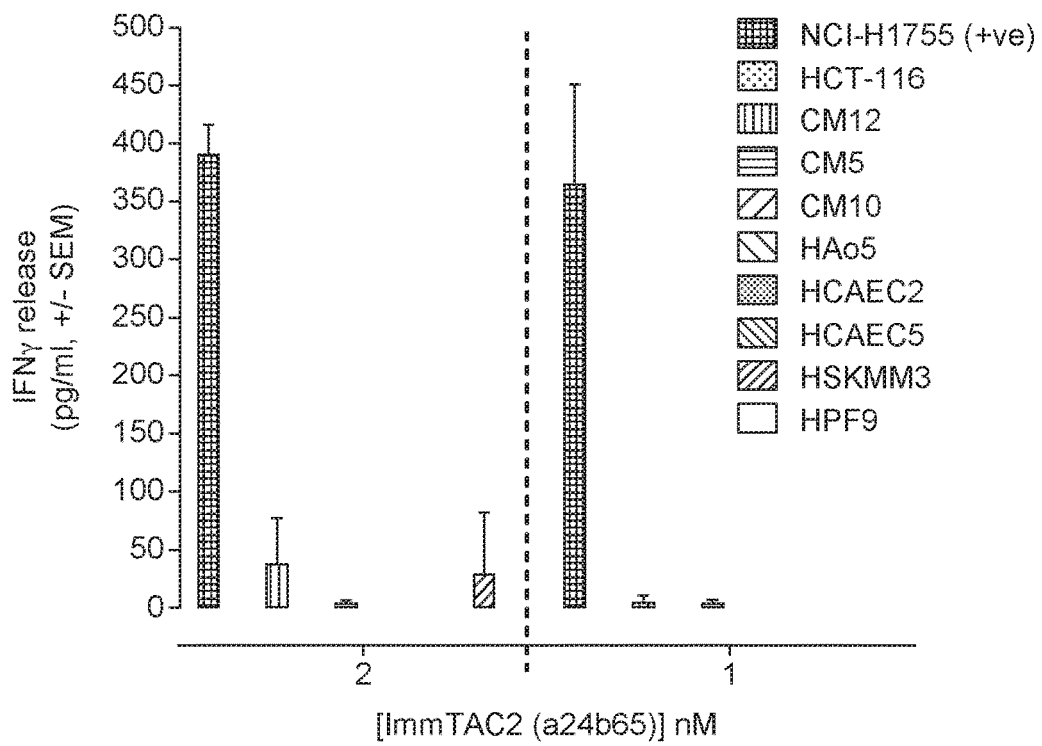
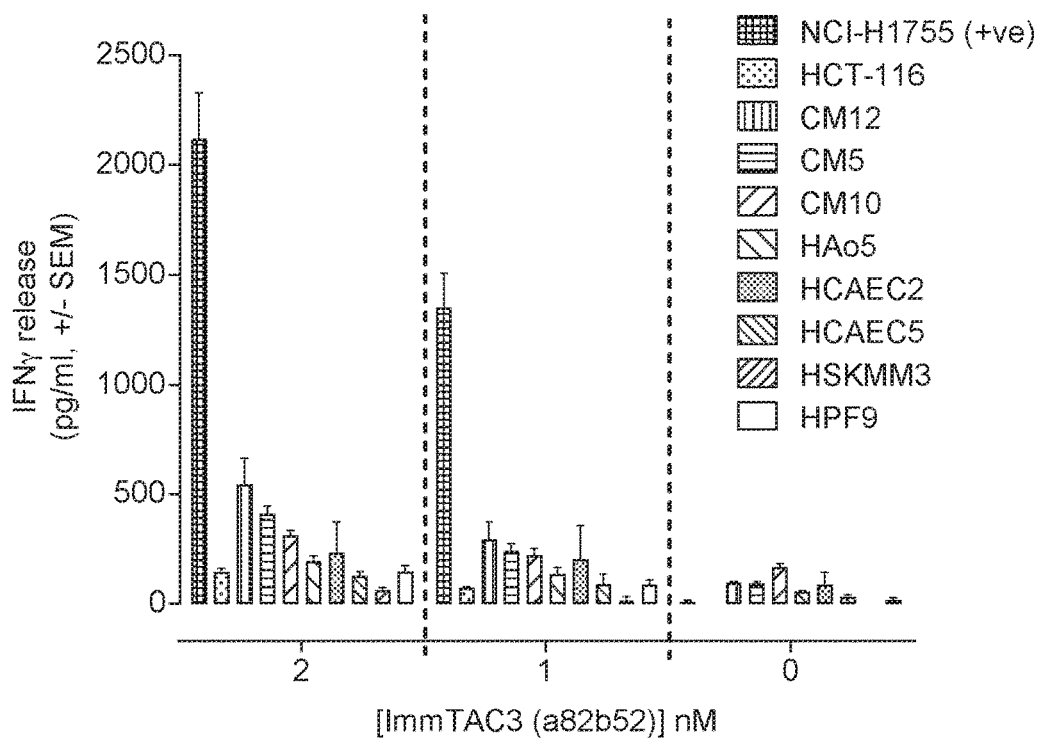
FIG. 11

SEQUENCE LISTING

<160> NUMBER OF SEQ ID NOS: 65

<210> SEQ ID NO 1
<211> LENGTH: 9
<212> TYPE: PRT
<213> ORGANISM: Homo sapiens

<400> SEQUENCE: 1

Ser Leu Leu Met Trp Ile Thr Gln Cys
1               5

<210> SEQ ID NO 2
<211> LENGTH: 211
<212> TYPE: PRT
<213> ORGANISM: Homo sapiens

<400> SEQUENCE: 2

Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
                20                  25                  30

Leu Phe Trp Tyr Val Gln Tyr Pro Asn Arg Gly Leu Gln Phe Leu Leu
            35                  40                  45

Lys Tyr Ile Thr Gly Asp Asn Leu Val Lys Gly Ser Tyr Gly Phe Glu
        50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys Ala Val Arg Asp Ile
                85                  90                  95

Asn Ser Gly Ala Gly Ser Tyr Gln Leu Thr Phe Gly Lys Gly Thr Lys
                100                 105                 110

Leu Ser Val Ile Pro Asn Ile Gln Asn Pro Asp Pro Ala Val Tyr Gln
            115                 120                 125

Leu Arg Asp Ser Lys Ser Ser Asp Lys Ser Val Cys Leu Phe Thr Asp
        130                 135                 140

Phe Asp Ser Gln Thr Asn Val Ser Gln Ser Lys Asp Ser Asp Val Tyr
145                 150                 155                 160

Ile Thr Asp Lys Thr Val Leu Asp Met Arg Ser Met Asp Phe Lys Ser
                165                 170                 175

Asn Ser Ala Val Ala Trp Ser Asn Lys Ser Asp Phe Ala Cys Ala Asn
                180                 185                 190

Ala Phe Asn Asn Ser Ile Ile Pro Glu Asp Thr Phe Phe Pro Ser Pro
            195                 200                 205

Glu Ser Ser
        210

<210> SEQ ID NO 3
<211> LENGTH: 245
<212> TYPE: PRT
<213> ORGANISM: Homo sapiens

<400> SEQUENCE: 3

Ser Ala Val Ile Ser Gln Lys Pro Ser Arg Asp Ile Cys Gln Arg Gly
1               5                   10                  15

Thr Ser Leu Thr Ile Gln Cys Gln Val Asp Ser Gln Val Thr Met Met
                20                  25                  30

Phe Trp Tyr Arg Gln Gln Pro Gly Gln Ser Leu Thr Leu Ile Ala Thr
            35                  40                  45

```
Ala Asn Gln Gly Ser Glu Ala Thr Tyr Glu Ser Gly Phe Val Ile Asp
             50                  55                  60

Lys Phe Pro Ile Ser Arg Pro Asn Leu Thr Phe Ser Thr Leu Thr Val
 65                  70                  75                  80

Ser Asn Met Ser Pro Glu Asp Ser Ser Ile Tyr Leu Cys Ser Val Gly
                 85                  90                  95

Gly Ser Gly Gly Ala Asp Thr Gln Tyr Phe Gly Pro Gly Thr Arg Leu
                100                 105                 110

Thr Val Leu Glu Asp Leu Lys Asn Val Phe Pro Pro Glu Val Ala Val
            115                 120                 125

Phe Glu Pro Ser Glu Ala Glu Ile Ser His Thr Gln Lys Ala Thr Leu
        130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Ser Thr Asp Pro Gln
                165                 170                 175

Pro Leu Lys Glu Gln Pro Ala Leu Asn Asp Ser Arg Tyr Cys Leu Ser
            180                 185                 190

Ser Arg Leu Arg Val Ser Ala Thr Phe Trp Gln Asn Pro Arg Asn His
        195                 200                 205

Phe Arg Cys Gln Val Gln Phe Tyr Gly Leu Ser Glu Asn Asp Glu Trp
210                 215                 220

Thr Gln Asp Arg Ala Lys Pro Val Thr Gln Ile Val Ser Ala Glu Ala
225                 230                 235                 240

Trp Gly Arg Ala Asp
                245

<210> SEQ ID NO 4
<211> LENGTH: 211
<212> TYPE: PRT
<213> ORGANISM: Homo sapiens

<400> SEQUENCE: 4

Ala Gln Ser Val Ala Gln Pro Glu Asp Gln Val Asn Val Ala Glu Gly
 1               5                  10                  15

Asn Pro Leu Thr Val Lys Cys Thr Tyr Ser Val Ser Gly Asn Pro Tyr
             20                  25                  30

Leu Phe Trp Tyr Val Gln Tyr Pro Asn Arg Gly Leu Gln Phe Leu Leu
         35                  40                  45

Lys Tyr Ile Thr Gly Asp Asn Leu Val Lys Gly Ser Tyr Gly Phe Glu
 50                  55                  60

Ala Glu Phe Asn Lys Ser Gln Thr Ser Phe His Leu Lys Lys Pro Ser
 65                  70                  75                  80

Ala Leu Val Ser Asp Ser Ala Leu Tyr Phe Cys Ala Val Arg Asp Ile
                 85                  90                  95

Asn Ser Gly Ala Gly Ser Tyr Gln Leu Thr Phe Gly Lys Gly Thr Lys
                100                 105                 110

Leu Ser Val Ile Pro Asn Ile Gln Asn Pro Asp Pro Ala Val Tyr Gln
            115                 120                 125

Leu Arg Asp Ser Lys Ser Ser Asp Lys Ser Val Cys Leu Phe Thr Asp
        130                 135                 140

Phe Asp Ser Gln Thr Asn Val Ser Gln Ser Lys Asp Ser Asp Val Tyr
145                 150                 155                 160

Ile Thr Asp Lys Cys Val Leu Asp Met Arg Ser Met Asp Phe Lys Ser
```

```
                    165                 170                 175

Asn Ser Ala Val Ala Trp Ser Asn Lys Ser Asp Phe Ala Cys Ala Asn
                180                 185                 190

Ala Phe Asn Asn Ser Ile Ile Pro Glu Asp Thr Phe Phe Pro Ser Pro
            195                 200                 205

Glu Ser Ser
        210

<210> SEQ ID NO 5
<211> LENGTH: 245
<212> TYPE: PRT
<213> ORGANISM: Homo sapiens

<400> SEQUENCE: 5

Ser Ala Val Ile Ser Gln Lys Pro Ser Arg Asp Ile Cys Gln Arg Gly
1               5                   10                  15

Thr Ser Leu Thr Ile Gln Cys Gln Val Asp Ser Gln Val Thr Met Met
            20                  25                  30

Phe Trp Tyr Arg Gln Gln Pro Gly Gln Ser Leu Thr Leu Ile Ala Thr
        35                  40                  45

Ala Asn Gln Gly Ser Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
                85                  90                  95

Gly Ser Gly Gly Ala Asp Thr Gln Tyr Phe Gly Pro Gly Thr Arg Leu
            100                 105                 110

Thr Val Leu Glu Asp Leu Lys Asn Val Phe Pro Pro Glu Val Ala Val
        115                 120                 125

Phe Glu Pro Ser Glu Ala Glu Ile Ser His Thr Gln Lys Ala Thr Leu
    130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Cys Thr Asp Pro Gln
                165                 170                 175

Pro Leu Lys Glu Gln Pro Ala Leu Asn Asp Ser Arg Tyr Ala Leu Ser
            180                 185                 190

Ser Arg Leu Arg Val Ser Ala Thr Phe Trp Gln Asp Pro Arg Asn His
        195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp
                245

<210> SEQ ID NO 6
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant alpha chain (a12)

<400> SEQUENCE: 6
```

Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
            20                  25                  30

Leu Phe Trp Tyr Val Gln Tyr Pro Asn Arg Gly Leu Gln Phe Leu Leu
            35                  40                  45

Lys Tyr Ile Thr Gly Asp Asn Leu Val Lys Gly Ser Tyr Gly Phe Glu
    50                  55                  60

Ala Glu Phe Asn Lys Ser Gln Thr Ser Phe His Leu Lys Lys Pro Ser
65              70                  75                  80

Ala Leu Val Ser Asp Ser Ala Leu Tyr Phe Cys Ala Val Arg Asp Ser
                85                  90                  95

Asp Gln His Ala Gly Ser Tyr Gln Leu Thr Phe Gly Lys Gly Thr Lys
            100                 105                 110

Leu Ser Val Ile Pro
        115

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant alpha chain (a24)

<400> SEQUENCE: 7

Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
            20                  25                  30

Leu Phe Trp Tyr Val Gln Tyr Pro Asn Arg Gly Leu Gln Phe Leu Leu
            35                  40                  45

Lys Tyr Leu Gly Asp Ser Ala Leu Val Lys Gly Ser Tyr Gly Phe Glu
    50                  55                  60

Ala Glu Phe Asn Lys Ser Gln Thr Ser Phe His Leu Lys Lys Pro Ser
65              70                  75                  80

Ala Leu Val Ser Asp Ser Ala Leu Tyr Phe Cys Ala Val Arg Asp Ile
                85                  90                  95

Asn Ser Gly Ala Gly Ser Tyr Gln Leu Thr Phe Gly Lys Gly Thr Lys
            100                 105                 110

Leu Ser Val Ile Pro
        115

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant alpha chain (a241)

<400> SEQUENCE: 8

Ala Gln Ser Val Ala Gln Pro Glu Asp Leu Val Asn Val Ala Glu Gly
1               5                   10                  15

Asn Pro Leu Thr Val Lys Cys Thr Tyr Ser Val Ser Gly Asn Pro Tyr

```
                    20                  25                  30

Leu Phe Trp Tyr Val Gln Tyr Pro Asn Arg Gly Leu Gln Phe Leu Leu
            35                  40                  45

Lys Tyr Leu Gly Asp Ser Ala Leu Val Lys Gly Ser Tyr Gly Phe Glu
        50                  55                  60

Ala Glu Phe Asn Lys Ser Gln Thr Ser Phe His Leu Lys Lys Pro Ser
 65                  70                  75                  80

Ala Leu Val Ser Asp Ser Ala Leu Tyr Phe Cys Ala Val Arg Asp Ile
                85                  90                  95

Asn Ser Gly Ala Gly Ser Tyr Gln Leu Thr Phe Gly Lys Gly Thr Lys
               100                 105                 110

Leu Ser Val Ile Pro
            115

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant alpha chain (a28)

<400> SEQUENCE: 9

Ala Gln Ser Val Ala Gln Pro Glu Asp Gln Val Asn Val Ala Glu Gly
 1               5                  10                  15

Asn Pro Leu Thr Val Lys Cys Thr Tyr Ser Val Ser Gly Asn Pro Tyr
                20                  25                  30

Leu Phe Trp Tyr Val Gln Tyr Pro Asn Arg Gly Leu Gln Phe Leu Leu
            35                  40                  45

Lys Tyr Ile Thr Gly Asp Asn Leu Val Lys Gly Ser Tyr Gly Phe Glu
        50                  55                  60

Ala Glu Phe Asn Lys Ser Gln Thr Ser Phe His Leu Lys Lys Pro Ser
 65                  70                  75                  80

Ala Leu Val Ser Asp Ser Ala Leu Tyr Phe Cys Ala Val Arg Ser Ser
                85                  90                  95

Arg Gln His Ala Gly Ser Tyr Gln Leu Thr Phe Gly Lys Gly Thr Lys
               100                 105                 110

Leu Ser Val Ile Pro
            115

<210> SEQ ID NO 10
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant alpha chain (a781)

<400> SEQUENCE: 10

Ala Gln Ser Val Ala Gln Pro Glu Asp Leu Val Asn Val Ala Glu Gly
 1               5                  10                  15

Asn Pro Leu Thr Val Lys Cys Thr Tyr Ser Val Ser Gly Asn Pro Tyr
                20                  25                  30

Leu Phe Trp Tyr Val Gln Tyr Pro Asn Arg Gly Leu Gln Phe Leu Leu
            35                  40                  45
```

```
Lys Tyr Leu Gly Asp Ser Ala Leu Val Lys Gly Ser Tyr Gly Phe Glu
    50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys Ala Val Arg Asp Ile
                85                  90                  95

Asp Ser Gly Ala Gly Ser Tyr Gln Leu Thr Phe Gly Lys Gly Thr Lys
            100                 105                 110

Leu Ser Val Ile Pro
        115

<210> SEQ ID NO 11
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant alpha chain (a821)

<400> SEQUENCE: 11

Ala Gln Ser Val Ala Gln Pro Glu Asp Leu Val Asn Val Ala Glu Gly
1               5                   10                  15

Asn Pro Leu Thr Val Lys Cys Thr Tyr Ser Val Ser Gly Asn Pro Tyr
            20                  25                  30

Leu Phe Trp Tyr Val Gln Tyr Pro Asn Arg Gly Leu Gln Phe Leu Leu
        35                  40                  45

Lys Tyr Leu Gly Asp Ser Ala Leu Val Lys Gly Ser Tyr Gly Phe Glu
    50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys Ala Val Arg Asp Ile
                85                  90                  95

Arg Ser Gly Ala Gly Ser Tyr Gln Leu Thr Phe Gly Lys Gly Thr Lys
            100                 105                 110

Leu Ser Val Ile Pro
        115

<210> SEQ ID NO 12
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant alpha chain (a82)

<400> SEQUENCE: 12

Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
            20                  25                  30

Leu Phe Trp Tyr Val Gln Tyr Pro Asn Arg Gly Leu Gln Phe Leu Leu
        35                  40                  45

Lys Tyr Leu Gly Asp Ser Ala Leu Val Lys Gly Ser Tyr Gly Phe Glu
    50                  55                  60

Ala Glu Phe Asn Lys Ser Gln Thr Ser Phe His Leu Lys Lys Pro Ser
65                  70                  75                  80
```

```
Ala Leu Val Ser Asp Ser Ala Leu Tyr Phe Cys Ala Val Arg Asp Ile
                85                  90                  95

Arg Ser Gly Ala Gly Ser Tyr Gln Leu Thr Phe Gly Lys Gly Thr Lys
            100                 105                 110

Leu Ser Val Ile Pro
        115

<210> SEQ ID NO 13
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant beta chain (b5)

<400> SEQUENCE: 13

Ser Ala Val Ile Ser Gln Lys Pro Ser Arg Asp Ile Lys Gln Arg Gly
1               5                   10                  15

Thr Ser Leu Thr Ile Gln Cys Gln Val Asp Ser Gln Val Thr Met Met
            20                  25                  30

Phe Trp Tyr Arg Gln Gln Pro Gly Gln Ser Pro Thr Leu Ile Ala Thr
        35                  40                  45

Ala Trp Thr Gly Gly Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
                85                  90                  95

Gly Ser Gly Gly Ala Asp Thr Gln Tyr Phe Gly Pro Gly Thr Arg Leu
            100                 105                 110

Thr Val Leu
        115

<210> SEQ ID NO 14
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant beta chain (b12)

<400> SEQUENCE: 14

Ser Ala Val Ile Ser Gln Lys Pro Ser Arg Asp Ile Lys Gln Arg Gly
1               5                   10                  15

Thr Ser Leu Thr Ile Gln Cys Gln Val Asp Lys Arg Leu Ala Leu Met
            20                  25                  30

Phe Trp Tyr Arg Gln Gln Pro Gly Gln Ser Pro Thr Leu Ile Ala Thr
        35                  40                  45

Ala Trp Thr Gly Gly Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
                85                  90                  95

Gly Ser Gly Gly Ala Asp Thr Gln Tyr Phe Gly Pro Gly Thr Arg Leu
```

Thr Val Leu
    115

<210> SEQ ID NO 15
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant beta chain (b52)

<400> SEQUENCE: 15

Ser Ala Val Ile Ser Gln Lys Pro Ser Arg Asp Ile Lys Gln Arg Gly
1               5                   10                  15

Thr Ser Leu Thr Ile Gln Cys Gln Val Asp Lys Arg Leu Ala Leu Met
            20                  25                  30

Phe Trp Tyr Arg Gln Gln Pro Gly Gln Ser Pro Thr Leu Ile Ala Thr
        35                  40                  45

Ala Trp Thr Gly Gly Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
                85                  90                  95

Gly Ser Gly Ala Ala Asp Thr Gln Tyr Phe Gly Pro Gly Thr Arg Leu
            100                 105                 110

Thr Val Leu
    115

<210> SEQ ID NO 16
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant beta chain (b56)

<400> SEQUENCE: 16

Ser Ala Val Ile Ser Gln Lys Pro Ser Arg Asp Ile Lys Gln Arg Gly
1               5                   10                  15

Thr Ser Leu Thr Ile Gln Cys Gln Val Asp Lys Arg Leu Ala Met Met
            20                  25                  30

Phe Trp Tyr Arg Gln Gln Pro Gly Gln Ser Pro Thr Leu Ile Ala Thr
        35                  40                  45

Ala Trp Thr Gly Gly Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
                85                  90                  95

Gly Ser Gly Gly Ala Asp Thr Gln Tyr Phe Gly Pro Gly Thr Arg Leu
            100                 105                 110

Thr Val Leu
    115

```
<210> SEQ ID NO 17
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant beta chain (b561)

<400> SEQUENCE: 17

Ser Ala Val Ile Ser Gln Lys Pro Ser Arg Asp Ile Lys Gln Arg Gly
1               5                   10                  15

Thr Ser Leu Thr Ile Gln Cys Gln Val Asp Lys Arg Leu Ala Met Met
            20                  25                  30

Phe Trp Tyr Arg Gln Gln Pro Gly Gln Ser Leu Thr Leu Ile Ala Thr
        35                  40                  45

Ala Trp Thr Gly Gly Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
                85                  90                  95

Gly Ser Gly Gly Ala Asp Thr Gln Tyr Phe Gly Pro Gly Thr Arg Leu
            100                 105                 110

Thr Val Leu
        115

<210> SEQ ID NO 18
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant beta chain (b65)

<400> SEQUENCE: 18

Ser Ala Val Ile Ser Gln Lys Pro Ser Arg Asp Ile Lys Gln Arg Gly
1               5                   10                  15

Thr Ser Leu Thr Ile Gln Cys Gln Val Asp Lys Arg Leu Ala Leu Met
            20                  25                  30

Phe Trp Tyr Arg Gln Gln Pro Gly Gln Ser Pro Thr Leu Ile Ala Thr
        35                  40                  45

Ala Trp Thr Gly Ser Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
                85                  90                  95

Gly Ser Gly Gly Ala Asp Thr Gln Tyr Phe Gly Pro Gly Thr Arg Leu
            100                 105                 110

Thr Val Leu
        115

<210> SEQ ID NO 19
<211> LENGTH: 115
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: Mutant beta chain (b651)

<400> SEQUENCE: 19

Ser Ala Val Ile Ser Gln Lys Pro Ser Arg Asp Ile Lys Gln Arg Gly
1               5                   10                  15

Thr Ser Leu Thr Ile Gln Cys Gln Val Asp Lys Arg Leu Ala Leu Met
            20                  25                  30

Phe Trp Tyr Arg Gln Gln Pro Gly Gln Ser Leu Thr Leu Ile Ala Thr
        35                  40                  45

Ala Trp Thr Gly Ser Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
                85                  90                  95

Gly Ser Gly Gly Ala Asp Thr Gln Tyr Phe Gly Pro Gly Thr Arg Leu
            100                 105                 110

Thr Val Leu
        115

<210> SEQ ID NO 20
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant beta chain (b67)

<400> SEQUENCE: 20

Ser Ala Val Ile Ser Gln Lys Pro Ser Arg Asp Ile Lys Gln Arg Gly
1               5                   10                  15

Thr Ser Leu Thr Ile Gln Cys Gln Val Asp Lys Arg Leu Ala Met Met
            20                  25                  30

Phe Trp Tyr Arg Gln Gln Pro Gly Gln Ser Pro Thr Leu Ile Ala Thr
        35                  40                  45

Ala Trp Thr Gly Gly Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
                85                  90                  95

Gly Ser Gly Ala Ala Asp Thr Gln Tyr Phe Gly Pro Gly Thr Arg Leu
            100                 105                 110

Thr Val Leu
        115

<210> SEQ ID NO 21
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant beta chain (b671)
```

<400> SEQUENCE: 21

Ser Ala Val Ile Ser Gln Lys Pro Ser Arg Asp Ile Lys Gln Arg Gly
1               5                   10                  15

Thr Ser Leu Thr Ile Gln Cys Gln Val Asp Lys Arg Leu Ala Met Met
            20                  25                  30

Phe Trp Tyr Arg Gln Gln Pro Gly Gln Ser Leu Thr Leu Ile Ala Thr
        35                  40                  45

Ala Trp Thr Gly Gly Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
                85                  90                  95

Gly Ser Gly Ala Ala Asp Thr Gln Tyr Phe Gly Pro Gly Thr Arg Leu
            100                 105                 110

Thr Val Leu
        115

<210> SEQ ID NO 22
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant beta chain (b68)

<400> SEQUENCE: 22

Ser Ala Val Ile Ser Gln Lys Pro Ser Arg Asp Ile Lys Gln Arg Gly
1               5                   10                  15

Thr Ser Leu Thr Ile Gln Cys Gln Val Asp Lys Arg Leu Ala Met Met
            20                  25                  30

Phe Trp Tyr Arg Gln Gln Pro Gly Gln Ser Pro Thr Leu Ile Ala Thr
        35                  40                  45

Ala Trp Thr Gly Ser Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
                85                  90                  95

Gly Ser Gly Gly Ala Asp Thr Gln Tyr Phe Gly Pro Gly Thr Arg Leu
            100                 105                 110

Thr Val Leu
        115

<210> SEQ ID NO 23
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant beta chain (b68l)

<400> SEQUENCE: 23

Ser Ala Val Ile Ser Gln Lys Pro Ser Arg Asp Ile Lys Gln Arg Gly
1               5                   10                  15

-continued

```
Thr Ser Leu Thr Ile Gln Cys Gln Val Asp Lys Arg Leu Ala Met Met
            20                  25                  30

Phe Trp Tyr Arg Gln Gln Pro Gly Gln Ser Leu Thr Leu Ile Ala Thr
        35                  40                  45

Ala Trp Thr Gly Ser Glu Ala Thr Tyr Glu Ser Gly Phe Val Ile Asp
50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
                85                  90                  95

Gly Ser Gly Gly Ala Asp Thr Gln Tyr Phe Gly Pro Gly Thr Arg Leu
            100                 105                 110

Thr Val Leu
        115

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 24

Gly Gly Gly Gly Ser
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 25

Gly Gly Gly Ser Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 26

Gly Gly Ser Gly Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: Linker sequence

<400> SEQUENCE: 27

Gly Ser Gly Gly Gly
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 28

Gly Ser Gly Gly Gly Pro
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 29

Gly Gly Glu Pro Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 30

Gly Gly Glu Gly Gly Gly Pro
1               5

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker sequence

<400> SEQUENCE: 31

Gly Gly Glu Gly Gly Gly Ser Glu Gly Gly Gly Ser
1               5                   10

<210> SEQ ID NO 32
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: ImmTAC alpha chain (comprising SEQ ID NO:
     7(a24) and the constant domain of SEQ ID NO: 4, truncated by 8
     amino acids)

<400> SEQUENCE: 32

Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
            20                  25                  30

Leu Phe Trp Tyr Val Gln Tyr Pro Asn Arg Gly Leu Gln Phe Leu Leu
        35                  40                  45

Lys Tyr Leu Gly Asp Ser Ala Leu Val Lys Gly Ser Tyr Gly Phe Glu
50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys Ala Val Arg Asp Ile
                85                  90                  95

Asn Ser Gly Ala Gly Ser Tyr Gln Leu Thr Phe Gly Lys Gly Thr Lys
            100                 105                 110

Leu Ser Val Ile Pro Asn Ile Gln Asn Pro Asp Pro Ala Val Tyr Gln
        115                 120                 125

Leu Arg Asp Ser Lys Ser Ser Asp Lys Ser Val Cys Leu Phe Thr Asp
130                 135                 140

Phe Asp Ser Gln Thr Asn Val Ser Gln Ser Lys Asp Ser Asp Val Tyr
145                 150                 155                 160

Ile Thr Asp Lys Cys Val Leu Asp Met Arg Ser Met Asp Phe Lys Ser
                165                 170                 175

Asn Ser Ala Val Ala Trp Ser Asn Lys Ser Asp Phe Ala Cys Ala Asn
            180                 185                 190

Ala Phe Asn Asn Ser Ile Ile Pro Glu Asp Thr
        195                 200

<210> SEQ ID NO 33
<211> LENGTH: 503
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: ImmTAC beta chain (comprising an anti-CD3 scFv
     fused via a linker to a TCR beta chain comprising SEQ ID NO:
     15(b52) and the constant domain of SEQ ID NO: 3)

<400> SEQUENCE: 33

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95
```

-continued

```
Thr Phe Gly Gln Gly Thr Lys Val Glu Ile Lys Gly Gly Gly Ser
                100                 105                 110
Gly Gly Gly Gly Ser Gly Gly Gly Ser Gly Gly Gly Ser Gly
            115                 120                 125
Gly Gly Ser Glu Val Gln Leu Val Glu Ser Gly Gly Gly Leu Val Gln
            130                 135                 140
Pro Gly Gly Ser Leu Arg Leu Ser Cys Ala Ala Ser Gly Tyr Ser Phe
145                 150                 155                 160
Thr Gly Tyr Thr Met Asn Trp Val Arg Gln Ala Pro Gly Lys Gly Leu
                165                 170                 175
Glu Trp Val Ala Leu Ile Asn Pro Tyr Lys Gly Val Ser Thr Tyr Asn
                180                 185                 190
Gln Lys Phe Lys Asp Arg Phe Thr Ile Ser Val Asp Lys Ser Lys Asn
            195                 200                 205
Thr Ala Tyr Leu Gln Met Asn Ser Leu Arg Ala Glu Asp Thr Ala Val
            210                 215                 220
Tyr Tyr Cys Ala Arg Ser Gly Tyr Tyr Gly Asp Ser Asp Trp Tyr Phe
225                 230                 235                 240
Asp Val Trp Gly Gln Gly Thr Leu Val Thr Val Ser Ser Gly Gly Gly
                245                 250                 255
Gly Ser Ser Ala Val Ile Ser Gln Lys Pro Ser Arg Asp Ile Lys Gln
            260                 265                 270
Arg Gly Thr Ser Leu Thr Ile Gln Cys Gln Val Asp Lys Arg Leu Ala
            275                 280                 285
Leu Met Phe Trp Tyr Arg Gln Gln Pro Gly Gln Ser Pro Thr Leu Ile
            290                 295                 300
Ala Thr Ala Trp Thr Gly Gly Glu Ala Thr Tyr Glu Ser Gly Phe Val
305                 310                 315                 320
Ile Asp Lys Phe Pro Ile Ser Arg Pro Asn Leu Thr Phe Ser Thr Leu
                325                 330                 335
Thr Val Ser Asn Met Ser Pro Glu Asp Ser Ser Ile Tyr Leu Cys Ser
            340                 345                 350
Val Gly Gly Ser Gly Ala Ala Asp Thr Gln Tyr Phe Gly Pro Gly Thr
            355                 360                 365
Arg Leu Thr Val Leu Glu Asp Leu Lys Asn Val Phe Pro Pro Glu Val
370                 375                 380
Ala Val Phe Glu Pro Ser Glu Ala Glu Ile Ser His Thr Gln Lys Ala
385                 390                 395                 400
Thr Leu Val Cys Leu Ala Thr Gly Phe Tyr Pro Asp His Val Glu Leu
                405                 410                 415
Ser Trp Trp Val Asn Gly Lys Glu Val His Ser Gly Val Cys Thr Asp
            420                 425                 430
Pro Gln Pro Leu Lys Glu Gln Pro Ala Leu Asn Asp Ser Arg Tyr Ala
            435                 440                 445
Leu Ser Ser Arg Leu Arg Val Ser Ala Thr Phe Trp Gln Asp Pro Arg
            450                 455                 460
Asn His Phe Arg Cys Gln Val Gln Phe Tyr Gly Leu Ser Glu Asn Asp
465                 470                 475                 480
Glu Trp Thr Gln Asp Arg Ala Lys Pro Val Thr Gln Ile Val Ser Ala
                485                 490                 495
Glu Ala Trp Gly Arg Ala Asp
                500
```

```
<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Heteroclitic NY-ESO-1 peptide

<400> SEQUENCE: 34

Ser Leu Leu Met Trp Ile Thr Gln Val
1               5

<210> SEQ ID NO 35
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ImmTAC alpha chain (comprising SEQ ID NO:
      7(a24) and the constant domain of SEQ ID NO: 4, truncated by 8
      amino acids)

<400> SEQUENCE: 35

Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
            20                  25                  30

Leu Phe Trp Tyr Val Gln Tyr Pro Asn Arg Gly Leu Gln Phe Leu Leu
        35                  40                  45

Lys Tyr Leu Gly Asp Ser Ala Leu Val Lys Gly Ser Tyr Gly Phe Glu
    50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys Ala Val Arg Asp Ile
                85                  90                  95

Asn Ser Gly Ala Gly Ser Tyr Gln Leu Thr Phe Gly Lys Gly Thr Lys
            100                 105                 110

Leu Ser Val Ile Pro Asn Ile Gln Asn Pro Asp Pro Ala Val Tyr Gln
        115                 120                 125

Leu Arg Asp Ser Lys Ser Ser Asp Lys Ser Val Cys Leu Phe Thr Asp
    130                 135                 140

Phe Asp Ser Gln Thr Asn Val Ser Gln Ser Lys Asp Ser Asp Val Tyr
145                 150                 155                 160

Ile Thr Asp Lys Cys Val Leu Asp Met Arg Ser Met Asp Phe Lys Ser
                165                 170                 175

Asn Ser Ala Val Ala Trp Ser Asn Lys Ser Asp Phe Ala Cys Ala Asn
            180                 185                 190

Ala Phe Asn Asn Ser Ile Ile Pro Glu Asp Thr
        195                 200

<210> SEQ ID NO 36
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ImmTAC beta chain (comprising an anti-CD3 scFv
``` fused via a linker to a TCR beta chain comprising SEQ ID NO:
18(b65) and the constant domain of SEQ ID NO: 5)

<400> SEQUENCE: 36

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Thr Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Ile Ser Val Asp Lys Ser Lys Asn
        195                 200                 205

Thr Ala Tyr Leu Gln Met Asn Ser Leu Arg Ala Glu Asp Thr Ala Val
210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
                245                 250                 255

Gly Ser Ser Ala Val Ile Ser Gln Lys Pro Ser Arg Asp Ile Lys Gln
            260                 265                 270

Arg Gly Thr Ser Leu Thr Ile Gln Cys Gln Val Asp Lys Arg Leu Ala
        275                 280                 285

Leu Met Phe Trp Tyr Arg Gln Gln Pro Gly Gln Ser Pro Thr Leu Ile
290                 295                 300

Ala Thr Ala Trp Thr Gly Ser Glu Ala Thr Tyr Glu Ser Gly Phe Val
305                 310                 315                 320

Ile Asp Lys Phe Pro Ile Ser Arg Pro Asn Leu Thr Phe Ser Thr Leu
                325                 330                 335

Thr Val Ser Asn Met Ser Pro Glu Asp Ser Ser Ile Tyr Leu Cys Ser
            340                 345                 350

Val Gly Gly Ser Gly Gly Ala Asp Thr Gln Tyr Phe Gly Pro Gly Thr
        355                 360                 365

Arg Leu Thr Val Leu Glu Asp Leu Lys Asn Val Phe Pro Pro Glu Val
370                 375                 380

Ala Val Phe Glu Pro Ser Glu Ala Glu Ile Ser His Thr Gln Lys Ala
385                 390                 395                 400
```

```
Thr Leu Val Cys Leu Ala Thr Gly Phe Tyr Pro Asp His Val Glu Leu
                405                 410                 415

Ser Trp Trp Val Asn Gly Lys Glu Val His Ser Gly Val Cys Thr Asp
            420                 425                 430

Pro Gln Pro Leu Lys Glu Gln Pro Ala Leu Asn Asp Ser Arg Tyr Ala
        435                 440                 445

Leu Ser Ser Arg Leu Arg Val Ser Ala Thr Phe Trp Gln Asp Pro Arg
    450                 455                 460

Asn His Phe Arg Cys Gln Val Gln Phe Tyr Gly Leu Ser Glu Asn Asp
465                 470                 475                 480

Glu Trp Thr Gln Asp Arg Ala Lys Pro Val Thr Gln Ile Val Ser Ala
                485                 490                 495

Glu Ala Trp Gly Arg Ala Asp
            500
```

<210> SEQ ID NO 37
<211> LENGTH: 203
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: ImmTAC alpha chain (comprising SEQ ID NO:
    12(a82) and the constant domain of SEQ ID NO: 4, truncated by 8
    amino acids)

<400> SEQUENCE: 37

```
Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
            20                  25                  30

Leu Phe Trp Tyr Val Gln Tyr Pro Asn Arg Gly Leu Gln Phe Leu Leu
        35                  40                  45

Lys Tyr Leu Gly Asp Ser Ala Leu Val Lys Gly Ser Tyr Gly Phe Glu
    50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys Ala Val Arg Asp Ile
                85                  90                  95

Arg Ser Gly Ala Gly Ser Tyr Gln Leu Thr Phe Gly Lys Gly Thr Lys
            100                 105                 110

Leu Ser Val Ile Pro Asn Ile Gln Asn Pro Asp Pro Ala Val Tyr Gln
        115                 120                 125

Leu Arg Asp Ser Lys Ser Ser Asp Lys Ser Val Cys Leu Phe Thr Asp
    130                 135                 140

Phe Asp Ser Gln Thr Asn Val Ser Gln Ser Lys Asp Ser Asp Val Tyr
145                 150                 155                 160

Ile Thr Asp Lys Cys Val Leu Asp Met Arg Ser Met Asp Phe Lys Ser
                165                 170                 175

Asn Ser Ala Val Ala Trp Ser Asn Lys Ser Asp Phe Ala Cys Ala Asn
            180                 185                 190

Ala Phe Asn Asn Ser Ile Ile Pro Glu Asp Thr
        195                 200
```

<210> SEQ ID NO 38
<211> LENGTH: 503

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ImmTAC beta chain (comprising an anti-CD3 scFv
      fused via a linker to a TCR beta chain comprising SEQ ID NO:
      15(b52) and the constant domain of SEQ ID NO: 5)

<400> SEQUENCE: 38

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Ser Glu Val Gln Leu Val Glu Ser Gly Gly Gly Leu Val Gln
130                 135                 140

Pro Gly Gly Ser Leu Arg Leu Ser Cys Ala Ala Ser Gly Tyr Ser Phe
145                 150                 155                 160

Thr Gly Tyr Thr Met Asn Trp Val Arg Gln Ala Pro Gly Lys Gly Leu
            165                 170                 175

Glu Trp Val Ala Leu Ile Asn Pro Tyr Lys Gly Val Ser Thr Tyr Asn
        180                 185                 190

Gln Lys Phe Lys Asp Arg Phe Thr Ile Ser Val Asp Lys Ser Lys Asn
    195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
            245                 250                 255

Gly Ser Ser Ala Val Ile Ser Gln Lys Pro Ser Arg Asp Ile Lys Gln
        260                 265                 270

Arg Gly Thr Ser Leu Thr Ile Gln Cys Gln Val Asp Lys Arg Leu Ala
    275                 280                 285

Leu Met Phe Trp Tyr Arg Gln Gln Pro Gly Gln Ser Pro Thr Leu Ile
    290                 295                 300

Ala Thr Ala Trp Thr Gly Gly Glu Ala Thr Tyr Glu Ser Gly Phe Val
305                 310                 315                 320

Ile Asp Lys Phe Pro Ile Ser Arg Pro Asn Leu Thr Phe Ser Thr Leu
            325                 330                 335

Thr Val Ser Asn Met Ser Pro Glu Asp Ser Ser Ile Tyr Leu Cys Ser
        340                 345                 350

Val Gly Gly Ser Gly Ala Ala Asp Thr Gln Tyr Phe Gly Pro Gly Thr
```

```
                    355                 360                 365
Arg Leu Thr Val Leu Glu Asp Leu Lys Asn Val Phe Pro Pro Glu Val
    370                 375                 380

Ala Val Phe Glu Pro Ser Glu Ala Glu Ile Ser His Thr Gln Lys Ala
385                 390                 395                 400

Thr Leu Val Cys Leu Ala Thr Gly Phe Tyr Pro Asp His Val Glu Leu
                    405                 410                 415

Ser Trp Trp Val Asn Gly Lys Glu Val His Ser Gly Val Cys Thr Asp
                420                 425                 430

Pro Gln Pro Leu Lys Glu Gln Pro Ala Leu Asn Asp Ser Arg Tyr Ala
                435                 440                 445

Leu Ser Ser Arg Leu Arg Val Ser Ala Thr Phe Trp Gln Asp Pro Arg
            450                 455                 460

Asn His Phe Arg Cys Gln Val Gln Phe Tyr Gly Leu Ser Glu Asn Asp
465                 470                 475                 480

Glu Trp Thr Gln Asp Arg Ala Lys Pro Val Thr Gln Ile Val Ser Ala
                485                 490                 495

Glu Ala Trp Gly Arg Ala Asp
                500

<210> SEQ ID NO 39
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ImmTAC alpha chain (comprising SEQ ID NO:
      12(a82) and the constant domain of SEQ ID NO: 4, truncated by 8
      amino acids)

<400> SEQUENCE: 39

Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
                20                  25                  30

Leu Phe Trp Tyr Val Gln Tyr Pro Asn Arg Gly Leu Gln Phe Leu Leu
            35                  40                  45

Lys Tyr Leu Gly Asp Ser Ala Leu Val Lys Gly Ser Tyr Gly Phe Glu
50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys Ala Val Arg Asp Ile
                85                  90                  95

Arg Ser Gly Ala Gly Ser Tyr Gln Leu Thr Phe Gly Lys Gly Thr Lys
                100                 105                 110

Leu Ser Val Ile Pro Asn Ile Gln Asn Pro Asp Pro Ala Val Tyr Gln
            115                 120                 125

Leu Arg Asp Ser Lys Ser Ser Asp Lys Ser Val Cys Leu Phe Thr Asp
        130                 135                 140

Phe Asp Ser Gln Thr Asn Val Ser Gln Ser Lys Asp Ser Asp Val Tyr
145                 150                 155                 160

Ile Thr Asp Lys Cys Val Leu Asp Met Arg Ser Met Asp Phe Lys Ser
                165                 170                 175

Asn Ser Ala Val Ala Trp Ser Asn Lys Ser Asp Phe Ala Cys Ala Asn
                180                 185                 190
```

Ala Phe Asn Asn Ser Ile Ile Pro Glu Asp Thr
          195                 200

<210> SEQ ID NO 40
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ImmTAC beta chain (comprising an anti-CD3 scFv
      fused via a linker to a TCR beta chain comprising SEQ ID NO:
      18(b65) and the constant domain of SEQ ID NO: 5)

<400> SEQUENCE: 40

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Thr Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Ile Ser Val Asp Lys Ser Lys Asn
        195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
                245                 250                 255

Gly Ser Ser Ala Val Ile Ser Gln Lys Pro Ser Arg Asp Ile Lys Gln
            260                 265                 270

Arg Gly Thr Ser Leu Thr Ile Gln Cys Gln Val Asp Lys Arg Leu Ala
        275                 280                 285

Leu Met Phe Trp Tyr Arg Gln Gln Pro Gly Gln Ser Pro Thr Leu Ile
    290                 295                 300

Ala Thr Ala Trp Thr Gly Ser Glu Ala Thr Tyr Glu Ser Gly Phe Val
305                 310                 315                 320

```
Ile Asp Lys Phe Pro Ile Ser Arg Pro Asn Leu Thr Phe Ser Thr Leu
            325                 330                 335

Thr Val Ser Asn Met Ser Pro Glu Asp Ser Ser Ile Tyr Leu Cys Ser
            340                 345                 350

Val Gly Gly Ser Gly Gly Ala Asp Thr Gln Tyr Phe Gly Pro Gly Thr
            355                 360                 365

Arg Leu Thr Val Leu Glu Asp Leu Lys Asn Val Phe Pro Pro Glu Val
            370                 375                 380

Ala Val Phe Glu Pro Ser Glu Ala Glu Ile Ser His Thr Gln Lys Ala
385                 390                 395                 400

Thr Leu Val Cys Leu Ala Thr Gly Phe Tyr Pro Asp His Val Glu Leu
            405                 410                 415

Ser Trp Trp Val Asn Gly Lys Glu Val His Ser Gly Val Cys Thr Asp
            420                 425                 430

Pro Gln Pro Leu Lys Glu Gln Pro Ala Leu Asn Asp Ser Arg Tyr Ala
            435                 440                 445

Leu Ser Ser Arg Leu Arg Val Ser Ala Thr Phe Trp Gln Asp Pro Arg
            450                 455                 460

Asn His Phe Arg Cys Gln Val Gln Phe Tyr Gly Leu Ser Glu Asn Asp
465                 470                 475                 480

Glu Trp Thr Gln Asp Arg Ala Lys Pro Val Thr Gln Ile Val Ser Ala
            485                 490                 495

Glu Ala Trp Gly Arg Ala Asp
            500

<210> SEQ ID NO 41
<211> LENGTH: 6
<212> TYPE: PRT
<213> ORGANISM: Homo sapiens

<400> SEQUENCE: 41

Val Ser Gly Asn Pro Tyr
1               5

<210> SEQ ID NO 42
<211> LENGTH: 8
<212> TYPE: PRT
<213> ORGANISM: Homo sapiens

<400> SEQUENCE: 42

Tyr Ile Thr Gly Asp Asn Leu Val
1               5

<210> SEQ ID NO 43
<211> LENGTH: 17
<212> TYPE: PRT
<213> ORGANISM: Homo sapiens

<400> SEQUENCE: 43

Cys Ala Val Arg Asp Ile Asn Ser Gly Ala Gly Ser Tyr Gln Leu Thr
1               5                   10                  15

Phe

<210> SEQ ID NO 44
<211> LENGTH: 5
<212> TYPE: PRT
<213> ORGANISM: Homo sapiens

<400> SEQUENCE: 44
```

```
Ser Gln Val Thr Met
1               5

<210> SEQ ID NO 45
<211> LENGTH: 7
<212> TYPE: PRT
<213> ORGANISM: Homo sapiens

<400> SEQUENCE: 45

Ala Asn Gln Gly Ser Glu Ala
1               5

<210> SEQ ID NO 46
<211> LENGTH: 14
<212> TYPE: PRT
<213> ORGANISM: Homo sapiens

<400> SEQUENCE: 46

Cys Ser Val Gly Gly Ser Gly Gly Ala Asp Thr Gln Tyr Phe
1               5                   10

<210> SEQ ID NO 47
<211> LENGTH: 17
<212> TYPE: PRT
<213> ORGANISM: Homo sapiens

<400> SEQUENCE: 47

Leu Phe Trp Tyr Val Gln Tyr Pro Asn Arg Gly Leu Gln Phe Leu Leu
1               5                   10                  15

Lys

<210> SEQ ID NO 48
<211> LENGTH: 33
<212> TYPE: PRT
<213> ORGANISM: Homo sapiens

<400> SEQUENCE: 48

Lys Gly Ser Tyr Gly Phe Glu Ala Glu Phe Asn Lys Ser Gln Thr Ser
1               5                   10                  15

Phe His Leu Lys Lys Pro Ser Ala Leu Val Ser Asp Ser Ala Leu Tyr
                20                  25                  30

Phe

<210> SEQ ID NO 49
<211> LENGTH: 17
<212> TYPE: PRT
<213> ORGANISM: Homo sapiens

<400> SEQUENCE: 49

Met Phe Trp Tyr Arg Gln Gln Pro Gly Gln Ser Leu Thr Leu Ile Ala
1               5                   10                  15

Thr

<210> SEQ ID NO 50
<211> LENGTH: 37
<212> TYPE: PRT
<213> ORGANISM: Homo sapiens

<400> SEQUENCE: 50

Thr Tyr Glu Ser Gly Phe Val Ile Asp Lys Phe Pro Ile Ser Arg Pro
1               5                   10                  15

Asn Leu Thr Phe Ser Thr Leu Thr Val Ser Asn Met Ser Pro Glu Asp
```

Ser Ser Ile Tyr Leu
         35

<210> SEQ ID NO 51
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant alpha chain (a86)

<400> SEQUENCE: 51

Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
            20                  25                  30

Leu Phe Trp Tyr Val Gln Tyr Pro Asn Arg Gly Leu Gln Phe Leu Leu
        35                  40                  45

Lys Tyr Leu Thr Asp Asp Asn Leu Val Lys Gly Ser Tyr Gly Phe Glu
    50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys Ala Val Arg Asp Ile
                85                  90                  95

Asn Ser Gly Ala Gly Ser Tyr Gln Leu Thr Phe Gly Lys Gly Thr Lys
            100                 105                 110

Leu Ser Val Ile Pro
        115

<210> SEQ ID NO 52
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant beta chain (b71)

<400> SEQUENCE: 52

Ser Ala Val Ile Ser Gln Lys Pro Ser Arg Asp Ile Lys Gln Arg Gly
1               5                   10                  15

Thr Ser Leu Thr Ile Gln Cys Gln Val Asp Ser Gln Val Ala Met Met
            20                  25                  30

Phe Trp Tyr Arg Gln Gln Pro Gly Gln Ser Pro Thr Leu Ile Ala Thr
        35                  40                  45

Ala Trp Gln Gly Ser Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
                85                  90                  95

Gly Ser Gly Ala Ala Asp Thr Gln Tyr Phe Gly Pro Gly Thr Arg Leu
            100                 105                 110

Thr Val Leu
        115

```
<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Ala Val Arg Asp Ser Asp Gln His Ala Gly Ser Tyr Gln Leu Thr
1               5                   10                  15

Phe

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Tyr Leu Gly Asp Ser Ala Leu Val
1               5

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Ala Val Arg Ser Ser Arg Gln His Ala Gly Ser Tyr Gln Leu Thr
1               5                   10                  15

Phe

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Ala Val Arg Asp Ile Asp Ser Gly Ala Gly Ser Tyr Gln Leu Thr
1               5                   10                  15

Phe

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Cys Ala Val Arg Asp Ile Arg Ser Gly Ala Gly Ser Tyr Gln Leu Thr
1               5                   10                  15

Phe
```

```
<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Tyr Leu Thr Asp Asp Asn Leu Val
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Arg Leu Ala Leu
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Trp Thr Gly Gly Glu Ala
1               5

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Ser Val Gly Gly Ser Gly Ala Ala Asp Thr Gln Tyr Phe
1               5                   10

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Arg Leu Ala Met
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63
```

```
Ala Trp Thr Gly Ser Glu Ala
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Gln Val Ala Met
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Trp Gln Gly Ser Glu Ala
1               5
```

T CELL RECEPTORS SPECIFIC FOR THE NY-ESO-1 TUMOR ANTIGEN-HLA-A*02 COMPLEX

CROSS-REFERENCE TO RELATED APPLICATIONS

This application is the National Stage of International Application No. PCT/GB2016/054032, filed Dec. 22, 2016, which claims the benefit of and priority to Great Britain Patent Application Serial No. 1522592.3, filed on Dec. 22, 2015, the contents of which are incorporated by reference in their entirety.

SEQUENCE LISTING

The instant application contains a Sequence Listing which has been filed electronically in ASCII format and is hereby incorporated by reference in its entirety. Said ASCII copy, created on Apr. 2, 2020, is named 40847US_CRF_sequence-listing.txt and is 66,076 bytes in size.

The present invention relates to T cell receptors (TCRs) which bind the HLA-A*02 restricted peptide SLLMWITQC (SEQ ID NO: 1) derived from the cancer antigen NY-ESO-1. Said TCRs may comprise mutations within the alpha and/or beta variable domains relative to a native NY-ESO-1 TCR. The TCRs of the invention are particularly suitable for use as novel immunotherapeutic reagents for the treatment of malignant disease.

BACKGROUND TO THE INVENTION

T cell receptors (TCRs) are naturally expressed by $CD4^+$ and $CD8^+$ T cells. TCRs are designed to recognize short peptide antigens that are displayed on the surface of antigen presenting cells in complex with Major Histocompatibility Complex (MHC) molecules (in humans, MHC molecules are also known as Human Leukocyte Antigens, or HLA) (Davis, et al., (1998), Annu Rev Immunol 16: 523-544.). $CD8^+$ T cells, which are also termed cytotoxic T cells, specifically recognize peptides bound to MHC class I and are generally responsible for finding and mediating the destruction of infected or cancerous cells.

NY-ESO-1 belongs to the family of germline encoded cancer antigens (Chen, et al., (1997), Cytogenet Cell Genet 79(3-4): 237-240: WO9814464) and has the Uniprot accession number P78358. Such germline antigens have been found to be frequently expressed in a variety of cancers, while their expression in normal tissues is limited to adult testes and other immune privileged sites. The cancer specific nature of these antigens makes them ideal targets for anti-cancer therapeutics. The precise function of NY-ESO-1 remains unknown but it's expression has been reported in foetal and adult testes (Satie, et al., (2002), Lab Invest 82(6): 775-780), ovary and uterine myometrium, as well as in a wide variety of cancers including myeloma (Andrade, et al., (2008), Cancer Immun 8: 2), ovarian cancer (Odunsi, et al., (2003), Cancer Res 63(18): 6076-6083), non-small cell lung cancer (Konishi, et al., (2004), Oncol Rep 11(5): 1063-1067) and melanoma (Barrow, et al., (2006), Clin Cancer Res 12(3 Pt 1): 764-771). The 9-mer peptide SLLMWITQC (SEQ ID NO 1) corresponds to amino acids 157-165 of the full length NY-ESO-1 protein. The same peptide is also found in LAGE-1A (Acc. No. 075638-2), an alternative cancer antigen (Lethe, et al., (1998), Int J Cancer 76(6): 903-908). This peptide binds to HLA-A*02 and the peptide-HLA complex is able to stimulate cytotoxic T cells leading to lysis of NY-ESO-1+, HLA-A*02+, tumour cells (Duffour, et al., (1999), Eur J Immunol 29(10): 3329-3337 and WO2000020445). The SLLMWITQC (SEQ ID NO: 1) HLA-A*02 complex therefore provides a useful target antigen for immunotherapeutic intervention.

The identification of particular TCR sequences that bind to SLLMWITQC (SEQ ID NO: 1) HLA-A*02 complex is advantageous for the development of novel immunotherapies. Such therapeutic TCRs may be used, for example, as soluble targeting agents for the purpose of delivering cytotoxic or immune effector agents to the tumour (Lissin, et al., (2013). "High-Affinity Monocloncal T-cell receptor (mTCR) Fusions. Fusion Protein Technologies for Biopharmaceuticals: Applications and Challenges". S. R. Schmidt, Wiley; Boulter, et al., (2003), Protein Eng 16(9): 707-711; Liddy, et al., (2012), Nat Med 8: 980-987), or alternatively they may be used to engineer T cells for adoptive therapy (June, et al., (2014), Cancer Immunol Immunother 63(9): 969-975). It is desirable that TCRs for immunotherapeutic use are able to strongly recognize the target antigen, by which it is meant that the TCR should possess a high affinity and/or long binding half-life for the target antigen in order to exert a potent response. TCRs as they exist in nature typically have low affinity for target antigen (low micromolar range), thus it is often necessary to identify mutations, including but not limited to substitutions, insertions and/or deletions, that can be made to a given TCR sequence in order to improve antigen binding. For use as soluble targeting agents TCR antigen binding affinities in the nanomolar to picomolar range and with binding half-lives of several hours are preferable. It is also desirable that therapeutic TCRs demonstrate a high level of specificity for the target antigen to mitigate the risk of toxicity in clinical applications resulting from off-target binding. Such high specificity may be especially challenging to obtain given the natural degeneracy of TCR antigen recognition (Wooldridge, et al., (2012), J Biol Chem 287(2): 1168-1177; Wilson, et al., (2004), Mol Immunol 40(14-15): 1047-1055). Finally, it is desirable that therapeutic TCRs are able to be expressed and purified in a highly stable form.

The TCR sequences defined herein are described with reference to IMGT nomenclature which is widely known and accessible to those working in the TCR field. For example, see: LeFranc and LeFranc, (2001). "T cell Receptor Factsbook", Academic Press; Lefranc, (2011), Cold Spring Harb Protoc 2011(6): 595-603; Lefranc, (2001), Curr Protoc Immunol Appendix 1: Appendix 1O; and Lefranc, (2003), Leukemia 17(1): 260-266. αβ TCRs consist of two disulphide linked chains. Each chain (alpha and beta) is generally regarded as having two domains, namely a variable and a constant domain. A short joining region connects the variable and constant domains and is typically considered part of the variable region. Additionally, the beta chain usually contains a short diversity region between the variable and joining regions.

The variable domain of each chain is located N-terminally and comprises three Complementarity Determining Regions (CDRs) embedded in a framework sequence. The CDRs comprise the recognition site for peptide-MHC binding. There are several genes coding for alpha chain variable (Vα) regions and several genes coding for beta chain variable (Vβ) regions. These genes are distinguished by their framework, CDR1 and CDR2 sequences, and by a partly defined CDR3 sequence. The Vα and Vβ genes are referred to in IMGT nomenclature by the prefixes 'TRAV' and 'TRBV' respectively (Folch and Lefranc, (2000), Exp Clin Immunogenet 17(1): 42-54; Scaviner and Lefranc, (2000), Exp Clin Immunogenet 17(2): 83-96; LeFranc and LeFranc, (2001), "T cell Receptor Factsbook", Academic Press). Likewise there are several joining or J genes, termed 'TRAJ' or 'TRBJ', for the alpha and beta chain respectively, and for the beta chain, a diversity or D gene termed 'TRBD' (Folch and Lefranc, (2000), Exp Clin Immunogenet 17(2): 107-114; Scaviner and Lefranc, (2000), Exp Clin Immunogenet 17(2): 97-106; LeFranc and LeFranc, (2001), "T cell Receptor Factsbook", Academic Press). The huge diversity of alpha and beta variable region sequences results from combinatorial rearrangements between the various V, J and D genes, which include allelic variants, and additional junctional diversity (Arstila, et al., (1999), Science 286(5441): 958-961; Robins et al., (2009), Blood 114(19): 4099-4107.) The constant, or C, regions of TCR alpha and beta chains are referred to as 'TRAC' and 'TRBC' respectively (Lefranc, (2001), Curr Protoc Immunol Appendix 1: Appendix 1O).

In the present specification and claims, the term "TCR alpha (or α) variable domain" refers to the concatenation of TRAV and TRAJ regions; a TRAV region only; or TRAV and a partial TRAJ region, and the term TCR alpha (or α) constant domain refers to the extracellular TRAC region, or to a C-terminal truncated or full length TRAC sequence. Likewise the term "TCR beta (or β) variable domain" may refer to the concatenation of TRBV and TRBD/TRBJ regions; to the TRBV and TRBD regions only; to the TRBV and TRBJ regions only; or to the TRBV and partial TRBD and/or TRBJ regions, and the term TCR beta (or β) constant domain refers to the extracellular TRBC region, or to a C-terminal truncated or full length TRBC sequence.

TCRs that target NY-ESO-1 have been previously reported (WO05113595; WO08039818; McCormack, et al., (2013), Cancer Immunol Immunother 62(4): 773-785).

The inventors have identified alternative TCR alpha and beta variable domain sequences that bind to the NY-ESO-1 HLA-A*02 complex. Such sequences are particularly suitable for use as therapeutic TCRs for targeted immunotherapy of cancers that present SLLMWITQC (SEQ ID NO: 1) HLA-A*02 complex.

The inventors have identified a native TCR comprising the following chain usage:

Alpha chain: TRAV3*01/TRAJ28*01
Beta chain: TRBV29-1*01/TRBD2*01/TRBJ2-3*01
(Note, the term '*01' indicates the allelic variant for this sequence, as designated by IMGT nomenclature)

This native TCR was used as a template from which the mutated sequences of the invention were derived.

SUMMARY OF INVENTION

The present invention provides as a first aspect a T cell receptor (TCR) having the property of binding to SLLMWITQC (SEQ ID NO: 1) HLA-A*02 complex and comprising a TCR alpha chain variable domain and/or a TCR beta chain variable domain, wherein
  the alpha chain variable domain comprises an amino acid sequence that has at least 90% identity, such as 90%, 91%, 92%, 93%, 94%, 95%, 96%, 97%, 98%, 99% or 100% identity, to amino acids 1-117 of SEQ ID NO: 2, and/or
  the beta chain variable domain comprises an amino acid sequence that has at least 90% identity, such as 90%, 91%, 92%, 93%, 94%, 95%, 96%, 97%, 98%, 99% or 100% identity, to amino acids 1-115 of SEQ ID NO: 3.

As a second aspect, the invention provides a TCR that binds to a SLLMWITQC (SEQ ID NO: 1) HLA-A*02 complex with an affinity greater than 50 μM, wherein: the alpha chain CDRs 1, 2 and 3 comprise SEQ ID NO: 41, 42 and 43 respectively, and/or the beta chain CDRs 1, 2 and 3 comprise SEQ ID NO: 44, 45 and 46 respectively; and/or at least one of the CDRs contains one or more conservative substitutions with respect to SEQ ID NO: 41 to 46; and/or at least one of the CDRs contains up to three tolerated substitutions with respect to SEQ ID NO: 41 to 46.

The alpha chain variable domain of the first or second aspect may have at least one of the following mutations with reference to the numbering of SEQ ID NO: 2:

| Residue no. | |
|---|---|
| I51 | L |
| T52 | G |
| G53 | D |
| D54 | S |
| N55 | A |
| D95 | S |
| I96 | S |
| N97 | D or R |
| S98 | Q |
| G99 | H | and/or the beta chain variable domain of the first or second aspect may have at least one of the following mutations with reference to the numbering of SEQ ID NO: 3:

| Residue no. | |
|---|---|
| S27 | K |
| Q28 | R |
| V29 | L |
| T30 | A |
| M31 | L |
| N50 | W |
| Q51 | T |
| S53 | G |
| G100 | A |

The alpha chain variable domain may have at least one of the following mutations with reference to the numbering of SEQ ID NO: 2:

| Residue no. | |
|---|---|
| I51 | L |
| G53 | D |

And/or the beta chain variable domain may have at least one of the following mutations with reference to the numbering of SEQ ID NO: 3:

| Residue no. | |
|---|---|
| T30 | A |
| N50 | W |
| G100 | A |

The alpha chain variable domain may have between 2 and 6 of the following mutations with reference to the numbering of SEQ ID NO: 2:

| Residue no. | |
|---|---|
| I51 | L |
| T52 | G |
| G53 | D |
| D54 | S |
| N55 | A |
| D95 | S |
| I96 | S |
| N97 | D or R |
| S98 | Q |
| G99 | H | and/or the beta chain variable domain may have between 3 and 9 of the following mutations with reference to SEQ ID NO: 3:

| Residue no. | |
|---|---|
| S27 | K |
| Q28 | R |
| V29 | L |
| T30 | A |
| M31 | L |
| N50 | W |
| Q51 | T |
| S53 | G |
| G100 | A |

The alpha chain variable domain may have at least one of the following groups of mutations
  Group 1: I51L, T52G, G53D, D54S, N55A
  Group 2: I51L, T52G, G53D, D54S, N55A, N97D
  Group 3: I51L, T52G, G53D, D54S, N55A, N97R
  Group 4: I96S, N97D, S98Q, G99H
  Group 5: D95S, I96S, N97R, S98Q, G99H
  Group 6: I51L, G53D
and/or the beta chain variable domain may have at least one of the following groups of mutations
  Group 1: N50W, Q51T, S53G
  Group 2: S27K, Q28R, V29L, T30A, M31L, N50W, Q51T, S53G
  Group 3: S27K, Q28R, V29L, T30A, M31L, N50W, Q51T, S53G, G100A
  Group 4: S27K, Q28R, V29L, T30A, N50W, Q51T
  Group 5: S27K, Q28R, V29L, T30A, N50W, Q51T S53G
  Group 6: S27K, Q28R, V29L, T30A, N50W, Q51T S53G, G100A
  Group 7: S27K, Q28R, V29L, T30A, M31L, N50W, Q51T
  Group 8: T30A, N50W, G100A
The alpha chain variable domain and beta chain variable domain may have the following groups of mutations, respectively:

| | alpha chain | | beta chain |
|---|---|---|---|
| Group 1 | I51L, T52G, G53D, D54S, N55A | Group 3 | S27K, Q28R, V29L, T30A, M31L, N50W, Q51T, S53G, G100A |
| Group 1 | I51L, T52G, G53D, D54S, N55A | Group 7 | S27K, Q28R, V29L, T30A, M31L, N50W, Q51T |
| Group 3 | I51L, T52G, G53D, D54S, N55A, N97R | Group 3 | S27K, Q28R, V29L, T30A, M31L, N50W, Q51T, S53G, G100A |
| Group 3 | I51L, T52G, G53D, D54S, N55A, N97R | Group 7 | S27K, Q28R, V29L, T30A, M31L, N50W, Q51T |

The TCR of the invention may comprise an alpha chain variable domain that has the following mutation with reference to the numbering of SEQ ID NO: 2:

| Residue no. | |
|---|---|
| Q10 | L | and/or the beta chain variable domain may have at least one of the following mutations with reference to the numbering of SEQ ID NO: 3:

| Residue no. | |
|---|---|
| C13 | K |
| L43 | P |

In the alpha chain variable domain the sequence of amino acid residues 27-32, 50-57 and 91-107 is selected from the following:

| Residues 27 - 32 | SEQ ID NO: | Residues 50 - 57 | SEQ ID NO: | Residues 91 - 107 | SEQ ID NO: |
|---|---|---|---|---|---|
| VSGNPY | 41 | YITGDNLV | 42 | CAVRDSDQHAGSYQLTF | 53 |
| VSGNPY | 41 | YLGDSALV | 54 | CAVRDINSGAGSYQLTF | 43 |
| VSGNPY | 41 | YITGDNLV | 42 | CAVRSSRQHAGSYQLTF | 55 |
| VSGNPY | 41 | YLGDSALV | 54 | CAVRDIDSGAGSYQLTF | 56 |
| VSGNPY | 41 | YLGDSALV | 54 | CAVRDIRSGAGSYQLTF | 57 |
| VSGNPY | 41 | YLTDDNLV | 58 | CAVRDINSGAGSYQLTF | 43 |

The TCR alpha chain variable domain may comprise an amino acid sequence that has at least 90% identity, such as 90%, 91%, 92%, 93%, 94%, 95%, 96%, 97%, 98%, 99% or 100% identity, to SEQ ID NO: 12.

In the beta chain variable domain the sequence of amino acid residues 27-31, 49-55 and 93-106 is selected from the following:

| Residues 27 - 31 | SEQ ID NO: | Residues 49 - 55 | SEQ ID NO: | Residues 93 - 106 | SEQ ID NO: |
|---|---|---|---|---|---|
| KRLAL | 59 | AWTGGEA | 60 | CSVGGSGGADTQYF | 46 |
| KRLAL | 59 | AWTGGEA | 60 | CSVGGSGAADTQYF | 61 |
| KRLAM | 62 | AWTGGEA | 60 | CSVGGSGGADTQYF | 46 |
| KRLAL | 59 | AWTGSEA | 63 | CSVGGSGGADTQYF | 46 |

-continued

| Residues 27 - 31 | SEQ ID NO: | Residues 49 - 55 | SEQ ID NO: | Residues 93 - 106 | SEQ ID NO: |
|---|---|---|---|---|---|
| KRLAM | 62 | AWTGGEA | 60 | CSVGGSGAADTQYF | 61 |
| KRLAM | 62 | AWTGSEA | 63 | CSVGGSGGADTQYF | 46 |
| SQVTM | 44 | AWTGGEA | 60 | CSVGGSGGADTQYF | 46 |
| SQVAM | 64 | AWQGSEA | 65 | CSVGGSGAADTQYF | 61 |

The TCR beta chain variable domain may comprise an amino acid sequence that has at least 90% identity, such as 90%, 91%, 92%, 93%, 94%, 95%, 96%, 97%, 98%, 99% or 100% identity, to SEQ ID NO: 15.

The alpha chain variable domain may have the sequence of amino acids residues 27-32, 50-57 and 91-107 and the beta chain variable domain may have the sequence of amino acid residues 27-31, 49-55 and 93-106 selected from the following:

| Alpha chain | | | | | | Beta Chain | | | | | |
|---|---|---|---|---|---|---|---|---|---|---|---|
| 27-32 | SEQ ID NO: | 50-57 | SEQ ID NO: | 91-107 | | 27-31 | SEQ ID NO: | 49-55 | SEQ ID NO: | 93-106 | SEQ ID NO: |
| VSGNPY | 41 | YLGDSALV | 54 | CAVRDIN-SGAGSYQLTF | | KRLAL | 43 | AWTGGEA | 60 | CSVGGSGAADTQYF | 61 |
| VSGNPY | 41 | YLGDSALV | 54 | CAVRDIN-SGAGSYQLTF | | KRLAL | 43 | AWTGSEA | 63 | CSVGGSGGADTQYF | 46 |
| VSGNPY | 41 | YLGDSALV | 54 | CAVRDIRSGAGSYQLTFKRLAL | 57 | | AWTGGEA | 60 | CSVGGSGAADTQYF | 61 |
| VSGNPY | 41 | YLGDSALV | 54 | CAVRDIRSGAGSYQLTFKRLAL | 57 | | AWTGSEA | 63 | CSVGGSGGADTQYF | 46 |

The alpha chain variable domain may comprise an amino acid sequence that has at least 90% identity, such as 90%, 91%, 92%, 93%, 94%, 95%, 96%, 97%, 98% or 100% identity to SEQ ID NO: 12 and the beta chain variable domain may comprise an amino acid sequence that has at least 90% identity, such as 90%, 91%, 92%, 93%, 94%, 95%, 96%, 97%, 98%, 99% or 100% identity to SEQ ID NO: 15.

The alpha chain variable domain may be selected from the amino acid sequence of SEQ ID NO: 6-12, or 51 and the beta chain variable domain may be selected from the amino acid sequence of SEQ ID NO: 13-23, or 52.

The alpha chain variable domain and the beta chain variable domain may be selected from the amino acid sequences of:

| Alpha chain variable domain | Beta chain variable domain |
|---|---|
| SEQ ID NO: 7 | SEQ ID NO: 15 |
| SEQ ID NO: 7 | SEQ ID NO: 18 |
| SEQ ID NO: 12 | SEQ ID NO: 15 |
| SEQ ID NO: 12 | SEQ ID NO: 18 |

The TCR of the invention may be an alpha-beta heterodimer, having an alpha chain TRAC constant domain sequence and a beta chain TRBC1 or TRBC2 constant domain sequence.

The alpha and beta chain constant domain sequences may be modified by truncation or substitution to delete the native disulphide bond between Cys4 of exon 2 of TRAC and Cys2 of exon 2 of TRBC1 or TRBC2 and/or the alpha and/or beta chain constant domain sequence(s) may be modified by substitution of cysteine residues for Thr 48 of TRAC and Ser 57 of TRBC1 or TRBC2, the said cysteines forming a non-native disulphide bond between the alpha and beta constant domains of the TCR.

The TCR of the invention may be in single chain format of the type Vα-L-Vβ, Vβ-L-Vα, Vα-Cα-L-Vβ, Vα-L-Vβ-Cβ, wherein Vα and Vβ are TCR α and β variable regions respectively, Cα and Cβ are TCR α and β constant regions respectively, and L is a linker sequence.

The TCR of the invention may be associated with a detectable label, a therapeutic agent or a PK modifying moiety.

The invention also provides a TCR anti-CD3 fusion comprising the TCR of the invention and an anti-CD3 antibody covalently linked to the C- or N-terminus of the alpha or beta chain of the TCR and such a TCR anti-CD3 fusion may comprise an alpha chain variable domain selected from any one of SEQ ID NO: 6-12, or 51 and a beta chain variable domain selected from any one of SEQ ID NO: 13-23, or 52. The beta chain may be linked to the anti-CD3 antibody sequence via a linker sequence; the linker sequence may be selected from the group consisting of GGGGS (SEQ ID NO: 24), GGGSG (SEQ ID NO: 25), GGSGG (SEQ ID NO: 26), GSGGG (SEQ ID NO: 27), GSGGGP (SEQ ID NO: 28), GGEPS (SEQ ID NO: 29), GGEGGGP (SEQ ID NO: 30), and GGEGGGSEGGGS (SEQ ID NO: 31).

The TCR anti-CD3 fusion of the invention may comprise an alpha chain amino acid sequence and beta chain amino acid sequence pairing that have at least 90% identity, such as 90%, 91%, 92%, 93%, 94%, 95%, 96%, 97%, 98%, 99% or 100% identity, to the amino acid sequence pairings as set forth in the table below.

| | alpha chain SEQ ID NO: | beta chain SEQ ID NO: | Shown in |
|---|---|---|---|
| ImmTAC1 | 32 | 33 | FIG. 5 |
| ImmTAC2 | 35 | 36 | FIG. 6 |
| ImmTAC3 | 37 | 38 | FIG. 7 |
| ImmTAC4 | 39 | 40 | FIG. 8 |

The invention also provides a nucleic acid encoding a TCR or the TCR anti-CD3 fusion of the invention.

Also provided is a non-naturally occurring and/or purified and/or engineered cell presenting a TCR or TCR anti-CD3 fusion of the invention a cell harbouring (a) a TCR expression vector which comprises nucleic acid of the invention in a single open reading frame, or two distinct open reading frames encoding the alpha chain and the beta chain respectively; or (b) a first expression vector which comprises nucleic acid encoding the alpha chain of a TCR or TCR anti-CD3 fusion of the invention, and a second expression vector which comprises nucleic acid encoding the beta chain of a TCR or TCR anti-CD3 fusion of the invention.

The cell presenting the TCR or TCR anti-CD3 fusion or the cell harbouring the expression vector(s) may be a T-cell.

The invention also provides a pharmaceutical composition comprising a TCR or TCR anti-CD3 fusion of the invention or a cell of the invention, together with one or more pharmaceutically acceptable carriers or excipients.

The TCR, TCR anti-CD3 fusion or a nucleic acid or a cell of the invention for use in medicine, is also provided. The TCR, TCR anti-CD3 fusion, cell or nucleic acid may be for use in a method of treating cancer in a human subject.

The human subject may have a tumour that expresses NY-ESO-1 and/or LAGE-1A and the tumour may be a solid tumour and be selected from a synovial sarcoma, non small cell lung carcinoma (NSCLC), bladder tumour, gastric tumour, prostate tumour, colorectal tumour, breast tumour, ovarian tumour, oesophageal tumour, melanoma, multiple myeloma, hepatocellular carcinoma and head and neck tumour. The human subject may be a subject of HLA-A*02 subtype.

DETAILED DESCRIPTION OF THE INVENTION

In a first aspect the invention provides a T cell receptor (TCR) having the property of binding to SLLMWITQC (SEQ ID NO: 1) HLA-A*02 complex and comprising a TCR alpha chain variable domain and/or a TCR beta chain variable domain, wherein the alpha chain variable domain comprises an amino acid sequence that has at least 90% identity, such as 90%, 91%, 92%, 93%, 94%, 95%, 96%, 97%, 98%, 99% or 100% identity, to amino acids 1-117 of SEQ ID NO: 2, and/or the beta chain variable domain comprises an amino acid sequence that has at least 90% identity, such as 90%, 91%, 92%, 93%, 94%, 95%, 96%, 97%, 98%, 99% or 100% identity, to amino acids 1-115 of SEQ ID NO: 3. The TCR may be isolated, cell free and/or soluble, i.e. it may not be a TCR that occurs in its natural state within a T-cell within a human body.

The invention also provides a TCR that binds to a SLLMWITQC (SEQ ID NO: 1) HLA-A*02 complex with an affinity greater than 50 μM, wherein: the alpha chain CDRs 1, 2 and 3 comprise SEQ ID NO: 41, 42 and 43 respectively, and/or the beta chain CDRs 1, 2 and 3 comprise SEQ ID NO: 44, 45 and 46 respectively; and/or at least one of the CDRs contains one or more conservative substitutions with respect to SEQ ID NO: 41 to 46; and/or at least one of the CDRs contains up to three tolerated substitutions with respect to SEQ ID NO: 41 to 46. The affinity of the TCRs for the SLLMWITQC (SEQ ID NO: 1) HLA-A*02 complex may be in the range 50 uM to 100 nM. Preferably said substitutions do not change the binding affinity by more than +/−50%, or more preferably by no more than +/−20%, relative the non-substituted TCR.

For the production of stable, soluble TCRs of the invention, a soluble version of the native TCR was used as starting sequence having the sequence shown in FIG. 2. For this purpose cysteine substitutions are introduced into the TRAC and TRBC regions such that a non-native interchain disulphide bond can be formed. Suitable positions for the location of said cysteine substitutions are described in WO03020763. FIG. 2 shows the extracellular sequences of the wild type TCR alpha and beta chains respectively, in soluble format. SEQ ID NO: 4 is identical to the native alpha chain extracellular sequence SEQ ID NO: 2 except that Thr48 of TRAC has been replaced with Cys. Likewise SEQ ID NO: 5 is identical to the native beta chain extracellular sequence SEQ ID NO: 3 except that Ser57 of TRBC has been replaced with Cys, Cys75 has been replaced with Ala and Asn201 has been replaced with Asp. The soluble wild-type TCR described above may be used to provide a reference against which the binding profile of mutated TCRs of the invention may be compared. A TCR of the first aspect may also be a TCR of the second aspect.

TCRs of either or both aspects the invention may be non-naturally occurring and/or purified and/or engineered. TCRs of the invention may have more than one mutation present in the alpha chain variable domain and/or the beta chain variable domain relative to the native NY-ESO-1 TCR.

"Engineered TCR" and "mutant TCR" are used synonymously herein and generally mean a TCR which has one or more mutations introduced relative to the wild-type NY-ESO-1 TCR, in particular in the alpha chain variable domain and/or the beta chain variable domain thereof. Mutations are preferably made within the CDR regions. These mutation(s) typically improve the binding affinity of the TCR to the SLLMWITQC (SEQ ID NO: 1) HLA-A*02 complex. The alpha chain variable domain may have at least one, two, three, four, five or six of the following mutations with reference to the numbering of SEQ ID NO: 2:

TABLE 1

| Residue no. | |
|---|---|
| I51 | L |
| T52 | G |
| G53 | D |
| D54 | S |
| N55 | A |
| D95 | S |
| I96 | S |
| N97 | D or R |
| S98 | Q |
| G99 | H | and/or the beta chain variable domain may have at least one, two, three, four, five, six, seven, eight or nine of the following mutations with reference to the numbering of SEQ ID NO: 3:

TABLE 2

| Residue no. | |
|---|---|
| S27 | K |
| Q28 | R |
| V29 | L |
| T30 | A |
| M31 | L |
| N50 | W |
| Q51 | T |
| S53 | G |
| G100 | A |

The alpha chain variable domain may have at least one of the following mutations with reference to the numbering of SEQ ID NO: 2:

TABLE 3

| Residue no. | |
|---|---|
| I51 | L |
| G53 | D |

And/or the beta chain variable domain may have at least one of the following mutations with reference to the numbering of SEQ ID NO: 3:

TABLE 4

| Residue no. | |
|---|---|
| T30 | A |
| N50 | W |
| G100 | A |

The alpha chain variable domain has at least one of the following groups of mutations
- Group 1: I51L, T52G, G53D, D54S, N55A
- Group 2: I51L, T52G, G53D, D54S, N55A, N97D
- Group 3: I51L, T52G, G53D, D54S, N55A, N97R
- Group 4: I96S, N97D, S98Q, G99H
- Group 5: D95S, I96S, N97R, S98Q, G99H
- Group 6: I51L, G53D and/or the beta chain variable domain has at least one of the following groups of mutations
- Group 1: N50W, Q51T, S53G
- Group 2: S27K, Q28R, V29L, T30A, M31L, N50W, Q51T, S53G
- Group 3: S27K, Q28R, V29L, T30A, M31L, N50W, Q51T, S53G, G100A
- Group 4: S27K, Q28R, V29L, T30A, N50W, Q51T
- Group 5: S27K, Q28R, V29L, T30A, N50W, Q51T S53G
- Group 6: S27K, Q28R, V29L, T30A, N50W, Q51T S53G, G100A
- Group 7: S27K, Q28R, V29L, T30A, M31L, N50W, Q51T
- Group 8: T30A, N50W, G100A Particular combinations of the groups of mutations may be as set out in the table below:

TABLE 5

| | alpha chain | | beta chain |
|---|---|---|---|
| Group 1 | I51L, T52G, G53D, D54S, N55A | Group 3 | S27K, Q28R, V29L, T30A, M31L, N50W, Q51T, S53G, G100A |
| Group 1 | I51L, T52G, G53D, D54S, N55A | Group 7 | S27K, Q28R, V29L, T30A, M31L, N50W, Q51T |
| Group 3 | I51L, T52G, G53D, D54S, N55A, N97R | Group 3 | S27K, Q28R, V29L, T30A, M31L, N50W, Q51T, S53G, G100A |
| Group 3 | I51L, T52G, G53D, D54S, N55A, N97R | Group 7 | S27K, Q28R, V29L, T30A, M31L, N50W, Q51T |

Particular combinations of mutations may be present in the TCR of the invention as set out in the tables below:

TABLE 6

Alpha Chain

| Residues 27-32 | SEQ ID NO: | Residues 50-57 | SEQ ID NO: | Residues 91-107 | SEQ ID NO: |
|---|---|---|---|---|---|
| VSGNPY | 41 | YITGDNLV | 42 | CAVRDSDQHAGSYQLTF | 53 |
| VSGNPY | 41 | YLGDSALV | 54 | CAVRDINSGAGSYQLTF | 43 |
| VSGNPY | 41 | YITGDNLV | 42 | CAVRSSRQHAGSYQLTF | 55 |
| VSGNPY | 41 | YLGDSALV | 54 | CAVRDIDSGAGSYQLTF | 56 |
| VSGNPY | 41 | YLGDSALV | 54 | CAVRDIRSGAGSYQLTF | 57 |
| VSGNPY | 41 | YLTDDNLV | 58 | CAVRDINSGAGSYQLTF | 43 |

TABLE 7

Beta Chain

| Residues 27-31 | SEQ ID NO: | Residues 49-55 | SEQ ID NO: | Residues 93-106 | SEQ ID NO: |
|---|---|---|---|---|---|
| KRLAL | 59 | AWTGGEA | 60 | CSVGGSGGADTQYF | 46 |
| KRLAL | 59 | AWTGGEA | 60 | CSVGGSGAADTQYF | 61 |
| KRLAM | 62 | AWTGGEA | 60 | CSVGGSGGADTQYF | 46 |
| KRLAL | 59 | AWTGSEA | 63 | CSVGGSGGADTQYF | 46 |
| KRLAM | 62 | AWTGGEA | 60 | CSVGGSGAADTQYF | 61 |
| KRLAM | 62 | AWTGSEA | 63 | CSVGGSGGADTQYF | 46 |
| SQVTM | 44 | AWTGGEA | 60 | CSVGGSGGADTQYF | 46 |
| SQVAM | 64 | AWQGSEA | 65 | CSVGGSGAADTQYF | 61 |

Particularly, the alpha and beta chain variable domains may comprise the following combinations of amino acid sequences:

TABLE 8

| Alpha chain | | | | | | Beta Chain | | | | | |
|---|---|---|---|---|---|---|---|---|---|---|---|
| 27-32 | SEQ ID NO: | 50-57 | SEQ ID NO: | 91-107 | SEQ ID NO: | 27-31 | SEQ ID NO: | 49-55 | SEQ ID NO: | 93-106 | SEQ ID NO: |
| VSGNPY | 41 | YLGDSALV | 54 | CAVRDINSGAGSYQLTF | 43 | KRLAL | 59 | AWTGGEA | 60 | CSVGGSGAADTQYF | 61 |
| VSGNPY | 41 | YLGDSALV | 54 | CAVRDINSGAGSYQLTF | 43 | KRLAL | 59 | AWTGSEA | 63 | CSVGGSGGADTQYF | 46 |
| VSGNPY | 41 | YLGDSALV | 54 | CAVRDIRSGAGSYQLTF | 57 | KRLAL | 59 | AWTGGEA | 60 | CSVGGSGAADTQYF | 61 |
| VSGNPY | 41 | YLGDSALV | 54 | CAVRDIRSGAGSYQLTF | 57 | KRLAL | 59 | AWTGSEA | 63 | CSVGGSGGADTQYF | 46 |

In certain embodiments, there are 1, 2, 3, 4, 5, 6, 7 or 8 mutations in alpha chain CDRs, for example 2 to 6 mutations, and/or 1, 2, 3, 4, 5, 6, 7, 8 or 9 mutations in the beta chain CDRs, for example 3 to 9 mutations. In some embodiments, the α chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues 1-117 of SEQ ID NO: 2, provided that the α chain variable domain has at least one of the mutations outlined above. In some embodiments, the β chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues 1-115 of SEQ ID NO: 3, provided that the β chain variable domain has at least one of the mutations outlined above. The alpha chain variable domain may comprise the amino acid sequence of any one of SEQ ID NO: 6-12 or 51 The beta chain variable domain may comprise the amino acid sequence of any one of SEQ ID NO: 13-23 or 52.

Mutations may also be made outside of the CDRs, such mutations may improve binding, but preferably improve purification yield and stability. Examples of such mutations in the alpha chain variable domain, with reference to the numbering of SEQ ID NO: 2 may be:

TABLE 9

| Residue no. | |
|---|---|
| Q10 | L | and/or in the beta chain variable domain may be at least one of the following mutations with reference to the numbering of SEQ ID NO: 3:

TABLE 10

| Residue no. | |
|---|---|
| C13 | K |
| L43 | P |

Mutations to a parental TCR may include those that are able to increase the binding affinity (kD and/or binding half life) of the TCR to SLLMWITQC (SEQ ID NO: 1). Mutations may include those that are able to reduce the amount of non-specific binding, i.e. reduce binding to antigens in addition to binding to SLLMWITQC (SEQ ID NO: 1), or increase the specificity of the TCR binding to SLLMWITQC (SEQ ID NO: 1). Mutations may include those that increase efficiency of folding and/or manufacture. Some mutations may contribute to each of these characteristics, others may contribute to affinity but not specificity, for example, or to specificity but not affinity etc.

Within the scope of the invention are phenotypically silent variants of any TCR of the invention disclosed herein. As used herein the term "phenotypically silent variants" is understood to refer to a TCR which incorporates one or more further amino acid changes in addition to those set out above which TCR has a similar phenotype to the corresponding TCR without said change(s). For the purposes of this application, TCR phenotype comprises antigen binding affinity (KD and/or binding half-life) and antigen specificity. A phenotypically silent variant may have a KD and/or binding half-life for the SLLMWITQC (SEQ ID NO: 1) HLA-A*02 complex within 20% of the measured KD and/or binding half-life of the corresponding TCR without said change(s), when measured under identical conditions (for example at 25° C. and on the same SPR chip). Suitable conditions are further defined in Example 3. Antigen specificity is further defined below. As is known to those skilled in the art, it may be possible to produce TCRs that incorporate changes in the variable domains thereof compared to those detailed above without altering the affinity of the interaction with the SLLMWITQC (SEQ ID NO: 1) HLA-A*02 complex. In particular, such silent mutations may be incorporated within parts of the sequence that are known not to be directly involved in antigen binding (e.g. outside the CDRs or parts of the CDRs that do not contact the peptide antigen). Such trivial variants are included in the scope of this invention. Those TCRs in which one or more conservative and/or tolerated substitutions have been made also form part of this invention. Tolerated substitutions are also phenotypically silent but may not be conservative, as defined below. Tolerated substitutions may result in a decrease in affinity for the SLLMWITQC (SEQ ID NO: 1) HLA-A*02 complex in comparison to a TCR not having a tolerated substitution. The decrease in affinity may be 5%, 10%, 15%, 20%, 25%, 30%, 40% or 50% of the TCR without the tolerated substitution. The decrease in affinity does not result in the affinity being less than (i.e. weaker than) 50 μm.

The TCRs of the present invention may also include one or more conservative substitutions which have a similar amino acid sequence and/or which retain the same function. The skilled person is aware that various amino acids have similar properties and thus are 'conservative'. One or more such amino acids of a protein, polypeptide or peptide can often be substituted by one or more other such amino acids without eliminating a desired activity of that protein, polypeptide or peptide.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions. The present invention therefore extends to use of a TCR comprising an amino acid sequence described above but with one or more conservative substitutions in the sequence, such that the amino acid sequence of the TCR has at least 90% identity, such as 90%, 91%, 92%, 93%, 94%, 95%, 96%, 97%, 98%, 99% or 100% identity, to the TCR comprising amino acids 1-117 of SEQ ID NOs: 2, 6-12 or 51 and/or amino acids 1-115 of SEQ ID NOs: 3, 13-23 or 52.

Particular combinations of the alpha chain variable domain and beta chain variable domain may be:

TABLE 11

| Alpha chain variable domain | Beta chain variable domain |
|---|---|
| SEQ ID NO: 7 | SEQ ID NO: 15 |
| SEQ ID NO: 7 | SEQ ID NO: 18 |
| SEQ ID NO: 12 | SEQ ID NO: 15 |
| SEQ ID NO: 12 | SEQ ID NO: 18 |

Amino acid changes relative to the sequences given above can be made using any suitable technique e.g. by using site-directed mutagenesis or solid state synthesis.

It should be appreciated that amino acid substitutions within the scope of the present invention can be made using naturally occurring or non-naturally occurring amino acids. For example, it is contemplated herein that the methyl group on an alanine may be replaced with an ethyl group, and/or that minor changes may be made to the peptide backbone. Whether or not natural or synthetic amino acids are used, it is preferred that only L-amino acids are present.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules. BLAST protein searches can be performed with the XBLAST program, score=50, wordlength=3 to obtain amino acid sequences homologous to protein molecules for use in the invention. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.).

When utilising BLAST, Gapped BLAST, and PSI-Blast programs, the default parameters of the respective programs (e.g.,) (BLAST and NBLAST) can be used. See ncbi.nlm.nih.gov. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

Mutations can be carried out using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) and restriction enzyme-based cloning, see Sambrook & Russell, (2001) Molecular Cloning—A Laboratory Manual ($3^{rd}$ Ed.) CSHL Press. Further information on ligation independent cloning (LIC) procedures can be found in Rashtchian, (1995) Curr Opin Biotechnol 6(1): 30-6.

The TCR of the second aspect may comprise an alpha chain framework 2 (FM2) region and an alpha chain framework 3 (FM3) region, wherein the FM2 and FM3 regions comprise SEQ ID NO: 47 and 48 respectively, and/or contain one or more conservative substitutions and/or up to three tolerated substitutions.

The TCR of the second aspect may comprise a beta chain FM2 region and a beta chain FM3 region, wherein the FM2 and FM3 regions comprise SEQ ID NOs:49 and 50 respectively, and/or contain one or more conservative substitutions and/or up to three tolerated substitutions.

The TCR of the second aspect may comprise amino acids 1-117 of SEQ ID NO: 2 and/or amino acids 1-115 of SEQ ID NO: 3, which each may contain one or more conservative substitutions and/or up to three tolerated mutations and/or one or more of the mutations defined in table 1 or table 2.

The TCRs of the invention have the property of binding the SLLMWITQC (SEQ ID NO: 1) HLA-A*02 complex. TCRs of the invention have been found to be highly specific for this epitope relative to other, irrelevant epitopes, and are thus particularly suitable as targeting vectors for delivery of therapeutic agents or detectable labels to cells and tissues displaying those epitopes. Specificity in the context of TCRs of the invention relates to their ability to recognise HLA-A*02 target cells that are positive for the peptide SLL-MWITQC (SEQ ID NO: 1), whilst having minimal ability to recognise HLA-A*02 target cells that are negative for the peptide. To test specificity the TCRs may be in soluble form and/or may be expressed on the surface of T cells. Recognition may be determined by measuring the level of T cell activation in the presence of a TCR and target cells. In this case, minimal recognition of peptide negative target cells is defined as a level of T cell activation of less than 20% preferably less than 10%, and more preferably less than 5%, of the level produced in the presence of peptide positive target cells, when measured under the same conditions. For soluble TCRs of the invention, specificity may be determined at a therapeutically relevant TCR concentration. A therapeutically relevant concentration may be defined as a TCR concentration of 10-9 M or below, and/or a concentration of up to 100, or up to 1000, fold greater than the corresponding EC50 value. Peptide positive cells may be obtained by peptide-pulsing or, more preferably, they may naturally present said peptide. Preferably, both peptide positive and peptide negative cells are human cells. Specificity can be measured, for example, in cellular assays such as those described in Examples 6-8. Specificity may additionally relate to the ability to bind to NY-ESO-1-HLA-A*02 complex and not multiple naturally-presented peptide HLA complexes, as determined by Biacore, for example. Preferably, binding to NY-ESO-1-HLA-A*02 complex is at least 400 fold greater than to other naturally-presented peptide HLA complexes.

TCRs of the invention may have a $K_D$ for the NY-ESO-1-HLA-A*02 complex of greater than (i.e. stronger than) 50 µM, for example between 50 µM and 1 pM. Certain TCRs of the invention may have a $K_D$ for the complex of from about 1 pM to about 50 nM, from about 1 pM to about 400 pM, from about 20 pM to about 200 pM. TCRs of the invention may have a binding half-life (T½) for the complex in the range of from about 1 sec to about 60 h or greater, from about 30 min to about 60 h or greater, or from about 6 h to about 60 h or greater. TCRs that are for use as soluble therapeutics and/or diagnostics when coupled to a detectable label or therapeutic agent preferably have a $K_D$ for the complex of from about 1 pM to about 200 pM, or from about 20 pM to about 100 pM, as determined using the BIAcore method of Example 3, and/or a binding half-life for the complex of from about 2 h to 60 h or greater, or from about 20 h to about 60 h or greater, as determined using the BIAcore method of Example 3. Certain TCRs of the invention may be suitable for adoptive therapy applications; such TCRs may have a $K_D$ for the complex of from about 50 nM to about 50 µM, or from about 100 nM to about 1 µM and/or a binding half-life for the complex of from about 3 sec to about 12 min.

Certain TCRs of the invention have a binding affinity for, and/or a binding half-life for, the SLLMWITQC (SEQ ID NO: 1)-HLA-A*02 complex substantially higher than that of the native TCR. Increasing the binding affinity of a native TCR often reduces the specificity of the TCR for its peptide-MHC ligand, and this is demonstrated in Zhao Yangbing et al., The Journal of Immunology, The American Association of Immunologists, US, vol. 179, No. 9, 1 Nov. 2007, 5845-5854. However, the TCRs of the invention may remain specific for the SLLMWITQC (SEQ ID NO: 1)-HLA-A*02 complex, despite having substantially higher binding affinity than the native TCR.

Binding affinity (inversely proportional to the equilibrium constant $K_D$) and binding half-life (expressed as T½) can be determined using the Surface Plasmon Resonance (BIAcore) and/or Octet method of Example 3 herein. It will be appreciated that doubling the affinity of a TCR results in halving the $K_D$. T½ is calculated as ln2 divided by the off-rate ($k_{off}$). Therefore, doubling of T½ results in a halving in $k_{off}$. $K_D$ and $k_{off}$ values for TCRs are usually measured for soluble forms of the TCR, i.e. those forms which are truncated to remove cytoplasmic and transmembrane domain residues. Preferably the binding affinity or binding half-life of a given TCR is measured several times, for example 3 or more times, using the same assay protocol and an average of the results is taken.

For use as a targeting agent for delivering therapeutic agents to the antigen presenting cell the TCR may be in soluble form (i.e. having no transmembrane or cytoplasmic domains). For stability, TCRs of the invention, and preferably soluble αβ heterodimeric TCRs, may have an introduced disulphide bond between residues of the respective constant domains, as described, for example, in WO 03/020763. One or both of the constant domains present in an αβ heterodimer of the invention may be truncated at the C terminus or C termini, for example by up to 15, or up to 10 or up to 8 or fewer amino acids. The C terminus of the alpha chain extracellular constant region may be truncated by 8 amino acids. For use in adoptive therapy, an αβ heterodimeric TCR may, for example, be transfected as full length chains having both cytoplasmic and transmembrane domains. TCRs for use in adoptive therapy may contain a disulphide bond corresponding to that found in nature between the respective alpha and beta constant domains, additionally or alternatively a non-native disulphide bond may be present.

The TCRs of the invention may be αβ heterodimers or may be in single chain format. Single chain formats include αβ TCR polypeptides of the Vα-L-Vβ, Vβ-L-Vα, Vα-Cα-L-Vβ or Vα-L-Vβ-Cβ types, wherein Vα and Vβ are TCR α and β variable regions respectively, Cα and Cβ are TCR α and β constant regions respectively, and L is a linker sequence. In certain embodiments single chain TCRs of the invention may have an introduced disulphide bond between residues of the respective constant domains, as described in WO 2004/033685. Single chain TCRs are further described in WO2004/033685; WO98/39482; WO01/62908; Weidanz et al. (1998) J Immunol Methods 221(1-2): 59-76; Hoo et al. (1992) Proc Natl Acad Sci USA 89(10): 4759-4763; Schodin (1996) Mol Immunol 33(9): 819-829).

As will be obvious to those skilled in the art, it may be possible to truncate the sequences provided at the C-terminus and/or N-terminus thereof, by 1, 2, 3, 4, 5 or more residues, without substantially affecting the binding characteristics of the TCR. All such trivial variants are encompassed by the present invention.

Alpha-beta heterodimeric TCRs of the invention usually comprise an alpha chain TRAC constant domain sequence and/or a beta chain TRBC1 or TRBC2 constant domain sequence. The alpha and beta chain constant domain sequences may be modified by truncation or substitution to delete the native disulphide bond between Cys4 of exon 2 of TRAC and Cys2 of exon 2 of TRBC1 or TRBC2. The alpha and/or beta chain constant domain sequence(s) may also be modified by substitution of cysteine residues for Thr 48 of TRAC and Ser 57 of TRBC1 or TRBC2, the said cysteines forming a disulphide bond between the alpha and beta constant domains of the TCR.

In a further aspect, the present invention provides nucleic acid encoding a TCR of the first and/or second aspect of the invention. In some embodiments, the nucleic acid is cDNA. In some embodiments, the invention provides nucleic acid comprising a sequence encoding an α chain variable domain of a TCR of the invention. In some embodiments, the invention provides nucleic acid comprising a sequence encoding a β chain variable domain of a TCR of the invention. The nucleic acid may be non-naturally occurring and/or purified and/or engineered.

In another aspect, the invention provides a vector which comprises nucleic acid of the invention. Preferably the vector is a TCR expression vector.

The invention also provides a cell harbouring a vector of the invention, preferably a TCR expression vector. The vector may comprise nucleic acid of the invention encoding in a single open reading frame, or two distinct open reading frames, the alpha chain and the beta chain respectively. Another aspect provides a cell harbouring a first expression vector which comprises nucleic acid encoding the alpha chain of a TCR of the invention, and a second expression vector which comprises nucleic acid encoding the beta chain of a TCR of the invention. Such cells are particularly useful in adoptive therapy. The cells of the invention may be isolated and/or recombinant and/or non-naturally occurring and/or engineered.

Since the TCRs of the invention have utility in adoptive therapy, the invention includes a non-naturally occurring and/or purified and/or or engineered cell, especially a T-cell, presenting a TCR of the invention. The invention also provides an expanded population of T cells presenting a TCR of the invention. There are a number of methods suitable for the transfection of T cells with nucleic acid (such as DNA, cDNA or RNA) encoding the TCRs of the invention (see for example Robbins et al., (2008) *J Immunol*. 180: 6116-6131). T cells expressing the TCRs of the invention will be suitable for use in adoptive therapy-based treatment of cancer. As will be known to those skilled in the art, there are a number of suitable methods by which adoptive therapy can be carried out (see for example Rosenberg et al., (2008) *Nat Rev Cancer* 8(4): 299-308).

Soluble TCRs of the invention are useful for delivering detectable labels or therapeutic agents to antigen presenting cells and tissues containing antigen presenting cells. They may therefore be associated (covalently or otherwise) with a detectable label (for diagnostic purposes wherein the TCR is used to detect the presence of cells presenting the SLL-MWITQC (SEQ ID NO: 1)-HLA-A*02 complex); a therapeutic agent; or a PK modifying moiety (for example by PEGylation).

Detectable labels for diagnostic purposes include for instance, fluorescent labels, radiolabels, enzymes, nucleic acid probes and contrast reagents.

Therapeutic agents which may be associated with the TCRs of the invention include immunomodulators, radioactive compounds, enzymes (perforin for example) or chemotherapeutic agents (cis-platin for example). To ensure that toxic effects are exercised in the desired location the toxin could be inside a liposome linked to a TCR so that the compound is released slowly. This will prevent damaging effects during transport in the body and ensure that the toxin has maximum effect after binding of the TCR to the relevant antigen presenting cells.

Other suitable therapeutic agents include:
small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E vincristine and doxorubicin;

peptide cytotoxins, i.e. proteins or fragments thereof with the ability to kill mammalian cells. For example, ricin, diphtheria toxin, *pseudomonas* bacterial exotoxin A, DNase and RNase;

radio-nuclides, i.e. unstable isotopes of elements which decay with the concurrent emission of one or more of α or β particles, or γ rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;

immuno-stimulants, i.e. immune effector molecules which stimulate immune response. For example, cytokines such as IL-2 and IFN-γ, Superantigens and mutants thereof;

TCR-HLA fusions, e.g. fusion to a peptide-HLA complex, wherein said peptide is derived from a common human pathogen, such as Epstein Barr Virus (EBV);

chemokines such as IL-8, platelet factor 4, melanoma growth stimulatory protein, etc;

antibodies or fragments thereof, including anti-T cell or NK cell determinant antibodies (e.g. anti-CD3, anti-CD28 or anti-CD16);

alternative protein scaffolds with antibody like binding characteristics complement activators;

xenogeneic protein domains, allogeneic protein domains, viral/bacterial protein domains, viral/bacterial peptides.

One preferred embodiment is provided by a TCR anti-CD3 fusion comprising a TCR of the invention associated (usually by fusion to the N- or C-terminus of the alpha or beta chain) with an anti-CD3 antibody, or a functional fragment or variant of said anti-CD3 antibody. (Such TCR-anti-CD3 fusions may be termed ImmTAC molecules). As used herein, the term TCR encompasses TCR-fusions, such as a TCR anti-CD3 fusion. As used herein, the term "antibody" encompasses such fragments and variants. Examples of anti-CD3 antibodies include but are not limited to OKT3, UCHT-1, BMA-031 and 12F6. Antibody fragments and variants/analogues which are suitable for use in the compositions and methods described herein include minibodies, Fab fragments, F(ab')₂ fragments, dsFv and scFv fragments, Nanobodies™ (these constructs, marketed by Ablynx (Belgium), comprise synthetic single immunoglobulin variable heavy domain derived from a camelid (e.g. camel or llama) antibody) and Domain Antibodies (Domantis (Belgium), comprising an affinity matured single immunoglobulin variable heavy domain or immunoglobulin variable light domain) or alternative protein scaffolds that exhibit antibody like binding characteristics such as Affibodies (Affibody (Sweden), comprising engineered protein A scaffold) or Anticalins (Pieris (Germany)), comprising engineered anticalins) to name but a few.

Linkage of the TCR and the anti-CD3 antibody may be direct, or indirect via a linker sequence. Linker sequences are usually flexible, in that they are made up primarily of amino acids such as glycine, alanine and serine which do not have bulky side chains likely to restrict flexibility. Usable or optimum lengths of linker sequences are easily determined. Often the linker sequence will be less than about 12, such as less than 10, or from 5-10 amino acids in length. Suitable linkers that may be used in TCR anti-CD3 fusions of the invention include, but are not limited to: GGGGS (SEQ ID NO: 24), GGGSG (SEQ ID NO: 25), GGSGG (SEQ ID NO: 26), GSGGG (SEQ ID NO: 27), GSGGGP (SEQ ID NO: 28), GGEPS (SEQ ID NO: 29), GGEGGGP (SEQ ID NO: 30), and GGEGGGSEGGGS (SEQ ID NO: 31) (as described in WO2010/133828).

Specific embodiments of anti-CD3-TCR fusion constructs of the invention include those alpha and beta chain pairings shown in the table below.

TABLE 7

|  | alpha chain SEQ ID NO: | beta chain SEQ ID NO: | Shown in |
| --- | --- | --- | --- |
| ImmTAC1 | 32 | 33 | FIG. 5 |
| ImmTAC2 | 35 | 36 | FIG. 6 |
| ImmTAC3 | 37 | 38 | FIG. 7 |
| ImmTAC4 | 39 | 40 | FIG. 8 |

A particularly preferred anti-CD3-TCR fusion comprises alpha chain SEQ ID NO: 37 and beta chain SEQ ID NO: 38.

For some purposes, the TCRs of the invention may be aggregated into a complex comprising several TCRs to form a multivalent TCR complex. There are a number of human proteins that contain a multimerisation domain that may be used in the production of multivalent TCR complexes. For example the tetramerisation domain of p53 which has been utilised to produce tetramers of scFv antibody fragments which exhibited increased serum persistence and significantly reduced off-rate compared to the monomeric scFv fragment (Willuda et al. (2001) J. Biol. Chem. 276 (17) 14385-14392). Haemoglobin also has a tetramerisation domain that could be used for this kind of application. A multivalent TCR complex of the invention may have enhanced binding capability for the SLLMWITQC (SEQ ID NO: 1)-HLA-A*02 complex compared to a non-multimeric wild-type or T cell receptor heterodimer of the invention. Thus, multivalent complexes of TCRs of the invention are also included within the invention. Such multivalent TCR complexes according to the invention are particularly useful for tracking or targeting cells presenting particular antigens in vitro or in vivo, and are also useful as intermediates for the production of further multivalent TCR complexes having such uses.

As is well-known in the art, TCRs may be subject to post translational modifications. Glycosylation is one such modification, which comprises the covalent attachment of oligosaccharide moieties to defined amino acids in the TCR chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e. oligosaccharide type, covalent linkage and total number of attachments) can influence protein function. Therefore, when producing recombinant proteins, controlling glycosylation is often desirable. Controlled glycosylation has been used to improve antibody based therapeutics. (Jefferis R., Nat Rev Drug Discov. 2009 March; 8(3):226-34.). For soluble TCRs of the invention glycosylation may be controlled in vivo, by using particular cell lines for example, or in vitro, by chemical modification. Such modifications are desirable, since glycosylation can improve phamacokinetics, reduce immunogenicity and more closely mimic a native human protein (Sinclair AM and Elliott S., Pharm Sci. 2005 August; 94(8):1626-35).

For administration to patients, the TCRs or TCR anti-CD3 fusions of the invention (preferably associated with a detectable label or therapeutic agent or expressed on a transfected T cell) or cells of the invention may be provided in a pharmaceutical composition together with one or more pharmaceutically acceptable carriers or excipients. Therapeutic or imaging TCRs, TCR fusions or cells, in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, such as parenteral (including subcutaneous, intramuscular, or intravenous), enteral (including oral or rectal), inhalation or intranasal routes. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. a suitable dose range for a soluble TCR of the invention associated with an anti-CD3 antibody may be between 25 ng/kg and 50 µg/kg. A physician will ultimately determine appropriate dosages to be used.

TCRs, pharmaceutical compositions, vectors, nucleic acids and cells of the invention may be provided in substantially pure form, for example at least 80%, at least 85%, at least 90%, at least 91%, at least 92%, at least 93%, at least 94%, at least 95%, at least 96%, at least 97%, at least 98%, at least 99% or 100% pure.

Also provided by the invention are:
A TCR, TCR anti-CD3 fusion, nucleic acid or cell of the invention for use in medicine, preferably for use in a method of treating cancer.
the use of a TCR, TCR anti-CD3 fusion, nucleic acid or cell of the invention in the manufacture of a medicament for treating cancer;
a method of treating cancer in a patient, comprising administering to the patient a TCR, TCR anti-CD3 fusion, nucleic acid, or cell of the invention.

The cancer to be treated may be a synovial sarcoma, non small cell lung carcinoma (NSCLC), bladder tumour, gastric tumour, prostate tumour, colorectal tumour, breast tumour, ovarian tumour, oesophageal tumour, melanoma, multiple myeloma, hepatocellular carcinoma and head and neck tumour.

Preferred features of each aspect of the invention are as for each of the other aspects mutatis mutandis. The prior art documents mentioned herein are incorporated to the fullest extent permitted by law.

The invention is described below with reference to the following non-limiting figures and examples, in which:

FIG. 1 provides amino acids sequences of the extracellular regions of native alpha and beta chain variable domains of the invention;

FIG. 2 provides amino acid sequences of the soluble extracellular regions of native alpha and beta chains of the invention;

FIG. 3 provides amino acid sequences of mutated TCR alpha chain variable regions of the invention;

FIG. 4 provides amino acid sequences of mutated TCR beta chain variable regions of the invention;

FIG. 5 provides amino acid sequences of ImmTAC molecules comprising TCR sequences of the invention;

FIG. 6 provides amino acid sequences of ImmTAC molecules comprising TCR sequences of the invention;

FIG. 7 provides amino acid sequences of ImmTAC molecules comprising TCR sequences of the invention;

FIG. 8 provides amino acid sequences of ImmTAC molecules comprising TCR sequences of the invention;

EXAMPLES

Figure 9:
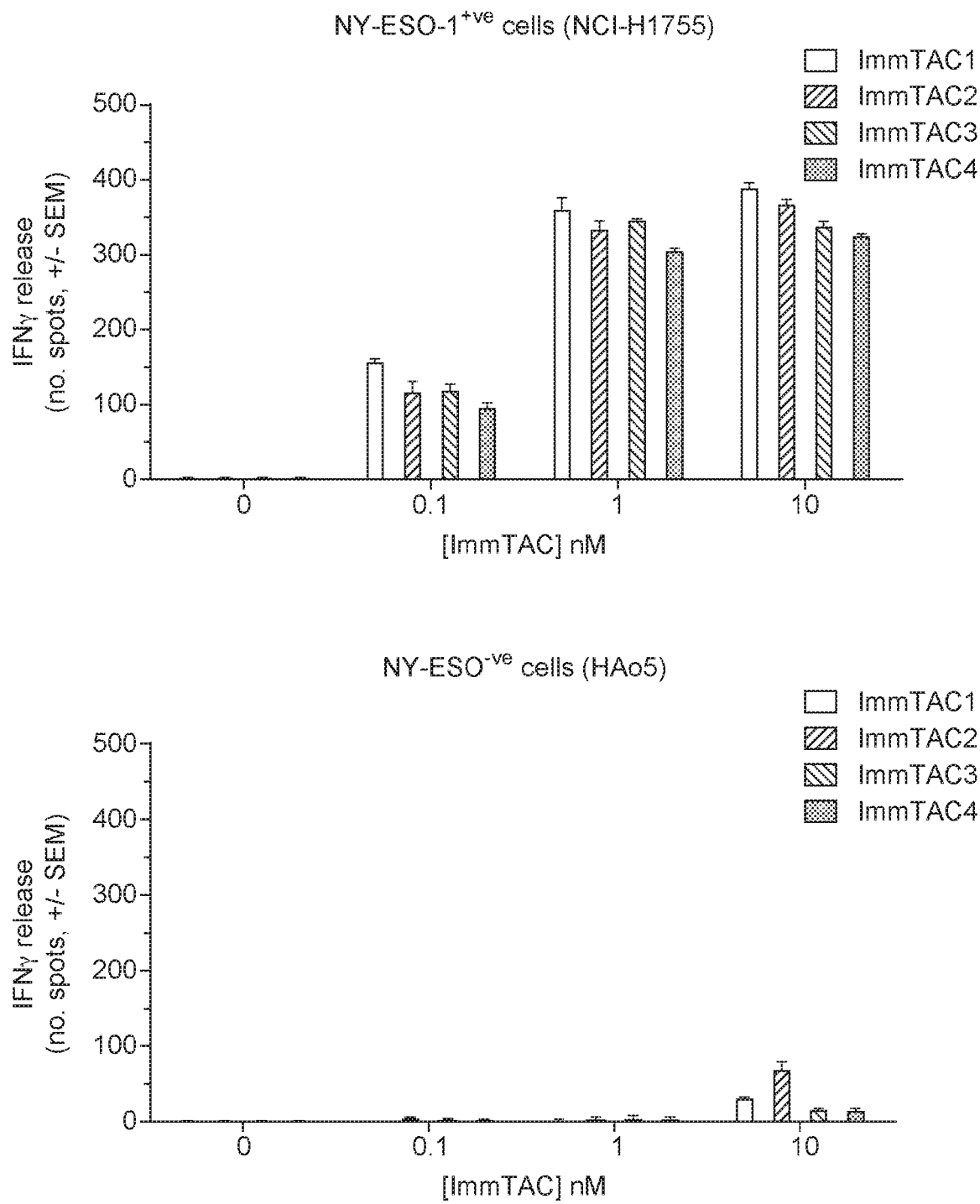
FIG. 9 shows potent and specific binding of ImmTAC molecules of the invention.

Example 1—Expression, Refolding and Purification of Soluble TCRs

DNA sequences encoding the alpha and beta extracellular regions of soluble TCRs of the invention were cloned separately into pGMT7-based expression plasmids using standard methods (as described in Sambrook, et al. *Molecular cloning*. Vol. 2. (1989) New York: Cold spring harbor laboratory press). The expression plasmids were transformed separately into *E. coli* strain Rosetta (BL21 pLysS), and single ampicillin-resistant colonies were grown at 37° C. in TYP (+ampicillin 100 μg/ml) medium to an $OD_{600}$ of ~0.6-0.8 before inducing protein expression with 0.5 mM IPTG. Cells were harvested three hours post-induction by centrifugation. Cell pellets were lysed with BugBuster protein extraction reagent (Merck Millipore) according to the manufacturer's instructions. Inclusion body pellets were recovered by centrifugation. Pellets were washed twice in Triton buffer (50 mM Tris-HCl pH 8.1, 0.5% Triton-X100, 100 mM NaCl, 10 mM NaEDTA) and finally resuspended in detergent free buffer (50 mM Tris-HCl pH 8.1, 100 mM NaCl, 10 mM NaEDTA). Inclusion body protein yield was quantified by solubilising with 6 M guanidine-HCl and measuring $OD_{280}$. Protein concentration was then calculated using the extinction coefficient. Inclusion body purity was measured by solubilising with 8M Urea and loading ~2 μg onto 4-20% SDS-PAGE under reducing conditions. Purity was then estimated or calculated using densitometry software (Chemidoc, Biorad). Inclusion bodies were stored at +4° C. for short term storage and at −20° C. or −70° C. for longer term storage.

For soluble TCR refolding, α and β chain-containing inclusion bodies were first mixed and diluted into 10 ml solubilisation/denaturation buffer (6 M Guanidine-hydrochloride, 50 mM Tris HCl pH 8.1, 100 mM NaCl, 10 mM EDTA, 20 mM DTT) followed by incubation for 30 min at 37° C. Refolding was then initiated by further dilution into 1 L of refold buffer (100 mM Tris pH 8.1, 400 mM L-Arginine HCL, 2 mM EDTA, 4 M Urea, 10 mM cysteamine hydrochloride and 2.5 mM cystamine dihydrochloride) and the solution mixed well. The refolded mixture was dialysed against 10 L $H_2O$ for 18-20 hours at 5° C.±3° C. After this time, the dialysis buffer was twice replaced with 10 mM Tris pH 8.1 (10 L) and dialysis continued for another 15 hours. The refold mixture was then filtered through 0.45 μm cellulose filters.

Purification of soluble TCRs was initiated by applying the dialysed refold onto an anion exchange column (POROS® 50HQ) and eluting bound protein with a gradient of 0-500 mM NaCl in 20 mM Tris pH 8.1 over 50 column volumes using an AKTA® purifier (GE Healthcare). Peak TCR fractions were identified by SDS PAGE before being pooled and concentrated. The concentrated sample was then applied to a SUPERDEX® 75HR gel filtration column (GE Healthcare) pre-equilibrated in Dulbecco's PBS buffer. The peak TCR fractions were pooled and concentrated and the final yield of purified material calculated.

Example 2—Expression, Refolding and Purification of ImmTAC Molecules (Soluble TCR-Anti CD3 Fusion Proteins)

ImmTAC preparation was carried out as described in Example 1, except that the TCR beta chain was fused via a linker to an anti-CD3 single chain antibody. In addition a cation exchange step was performed during purification following the anion exchange. In this case the peak fractions from anion exchange were diluted 20 fold in 20 mM IVIES (pH6.5), and applied to a cation exchange column (POROS® 50HS). Bound protein was eluted with a gradient of 0-500 mM NaCl in 20 mM IVIES. Peak ImmTAC fractions were pooled and adjusted to 50 mM Tris pH 8.1, before being concentrated and applied directly to the gel filtration matrix as described in Example 1.

Example 3—Binding Characterisation

Binding analysis of purified soluble TCRs and ImmTAC molecules to the relevant peptide-HLA complex was carried out by surface plasmon resonance, using a BIAcore 3000 or BIAcore T200 instrument, or by biolayer interferometry, using a ForteBio Octet instrument). Biotinylated class I HLA-A*02 molecules were refolded with the peptide of interest and purified using methods known to those in the art (O'Callaghan et al. (1999). Anal Biochem 266(1): 9-15; Garboczi, et al. (1992). Proc Natl Acad Sci USA 89(8): 3429-3433). All measurements were performed at 25° C. in Dulbecco's PBS buffer, supplemented with 0.005% P20.
BIAcore Biotinylated peptide-HLA monomers were immobilized on to streptavidin-coupled CM-5 sensor chips. Equilibrium binding constants were determined using serial dilutions of soluble TCR/ImmTAC injected at a constant flow rate of 30 μl min⁻¹ over a flow cell coated with ~200 response units (RU) of peptide-HLA-A*02 complex. Equilibrium responses were normalised for each TCR concentration by subtracting the bulk buffer response on a control flow cell containing an irrelevant peptide-HLA. The $K_D$ value was obtained by non-linear curve fitting using Prism software and the Langmuir binding isotherm, bound=C*Max/(C+ KD), where "bound" is the equilibrium binding in RU at injected TCR concentration C and Max is the maximum binding.

For high affinity interactions, binding parameters were determined by single cycle kinetics analysis. Five different concentrations of soluble TCR/ImmTAC were injected over a flow cell coated with ~100-200 RU of peptide-HLA complex using a flow rate of 50-60 μl min⁻¹. Typically, 60-120 μl of soluble TCR/ImmTAC was injected at a top concentration of 100-200 nM, with successive 2 fold dilutions used for the other four injections. The lowest concentration was injected first. To measure the dissociation phase buffer was then injected until ≥10% dissociation occurred, typically after 1-3 hours. Kinetic parameters were calculated using BIAevaluation® software. The dissociation phase was fitted to a single exponential decay equation enabling calculation of half-life. The equilibrium constant $K_D$ was calculated from $k_{off}/k_{on}$.

Octet

Biotinylated peptide-HLA monomers were captured to 1 nm on to (SA) streptavidin biosensors (Pall ForteBio) pre-immobilised with streptavidin. The sensors were blocked with free biotin (2 μM) for 2 minutes. Equilibrium binding constants were determined by immersing the loaded biosensors into soluble TCR/ImmTAC serially diluted in a 96-well or 384-well sample plate. Plate shaking was set to 1000 rpm. For low affinity interactions (μM range) a short association (~2 minutes) and a short dissociation time (~2 minutes) was used. Binding curves were processed by double reference subtraction of reference biosensors loaded with irrelevant pHLA using Octet Data Analysis Software (Pall ForteBio). Responses (nm) at equilibrium were used to estimate the $K_D$ value from steady state plots fitted to the equation Response=Rmax*conc/(KD+conc), where "response" is the equilibrium binding in nm at each TCR concentration (conc) and Rmax is the maximum binding response at pHLA saturation.

For high affinity interactions (nM-pM range), kinetic parameters were determined from binding curves at ≥3 TCR/ImmTAC concentrations typically 10 nM, 5 nM and 2.5 nM. The association time was 30 minutes and the dissociation time 1-2 hours. Binding curves were processed by double reference subtraction of reference biosensors loaded with irrelevant pHLA and blocked with biotin. Kinetic parameters $k_{on}$ and $k_{off}$ were calculated by global fitting directly to the binding curves using Octet Data Analysis Software (Pall ForteBio). $K_D$ was calculated from $k_{off}/k_{on}$ and the dissociation half-life was calculated from $t_{1/2}=0.693/k_{off}$.

Example 4—Binding Characterisation of a Soluble Non-Mutated TCR of the Invention A soluble wild-type TCR was prepared according to the methods described in Example 1 and binding to pHLA analysed according to Example 3. The amino acid sequences of the alpha and beta chains corresponded to those shown in FIG. 2. Soluble biotinylated HLA-A*02 was prepared with either the wild-type (SLLMWITQC (SEQ ID NO: 1)) or heteroclitic NY-ESO-1 peptide (SLLMWITQV SEQ ID NO: 34), and immobilised onto a BIAcore sensor chip. KD values were determined to be 5.2 μM and 4.3 μM respectively. No significant binding was detected against 15 irrelevant peptide HLA-A*02 complexes.

These data indicate that the TCR binds to the target with a suitable affinity and specificity. These TCR chains therefore provide a useful scaffold for the identification of further TCRs of the invention.

Example 5—Binding Characterisation Soluble High Affinity TCRs and ImmTAC Molecules of the Invention Soluble mutated TCRs and ImmTAC molecules were prepared as described in Examples 1 and 2, and binding characteristics determined according to Example 3. The TCR alpha and or beta chains contained mutations in at least one CDR region relative to the CDR sequences shown in FIG. 2 (SEQ ID NOs:41 to 46). The amino acid sequences of certain mutated TCR alpha and beta chain variable regions of the invention are provided in FIGS. 4 and 5 respectively. The table below provides binding characteristics for soluble TCRs and/or ImmTAC molecules comprising the indicated alpha and beta variable regions. Binding was measured using the heteroclitic NY-ESO-1 peptide (SLLMWITQV (SEQ ID NO: 34)).

| Alpha chain SEQ ID NO: | Beta chain SEQ ID NO: | Format (soluble/ ImmTAC) | Method (Biacore/ Octet) | Binding parameters | |
|---|---|---|---|---|---|
| | | | | KD | $T_{1/2}$ |
| (a12) 6 | (b12) 14 | ImmTAC | Biacore | 202 pM | 19.2 h |
| (a12) 6 | (b5) 13 | soluble | Biacore | 1.5 nM | 163.6 min |
| (a12) 6 | (b52) 15 | ImmTAC | Biacore | 244 pM | 14.2 h |
| 2 | (b5) 13 | soluble | Octet | nd | 1.3 min |
| 2 | (b12) 14 | soluble | Biacore | 3.8 nM | 72.33 min |
| 2 | (b12) 14 | ImmTAC | Biacore | 1.6 nM | 1.92 h |
| (a24I) 8 | (b52) 15 | ImmTAC | Biacore | 65 pM | 33.54 h |
| (a24I) 8 | (b65I) 19 | ImmTAC | Octet | 324 pM | 8.71 h |
| (a24I) 8 | (b12) 14 | ImmTAC | Biacore | 125 pM | 17.9 h |
| (a24I) 8 | (b65) 18 | ImmTAC | Octet | 325 pM | 6.8 h |
| (a24I) 8 | (b56) 16 | ImmTAC | Octet | 253 pM | 6.65 h |
| (a24I) 8 | (b56I) 17 | ImmTAC | Octet | 249 pM | 9.05 h |
| (a24I) 8 | (b67) 20 | ImmTAC | Octet | 252 pM | 9.49 h |
| (a24I) 8 | (b67I) 21 | ImmTAC | Octet | 256 pM | 10.08 h |
| (a24I) 8 | (b68) 22 | ImmTAC | Octet | 273 pM | 7.38 h |
| (a24I) 8 | (b68I) 23 | ImmTAC | Octet | 303 pM | 6.59 h |
| (a24I) 8 | (b5) 13 | soluble | Biacore | 2.7 nM | 54.8 min |
| (a24) 7 | (b52) 15 | ImmTAC[1] | Biacore | 18.6 pM | 78 h |
| (a24) 7 | (b65) 18 | ImmTAC[2] | Biacore | 76 pM | 24.2 h |
| (a28) 9 | (b12) 14 | ImmTAC | Biacore | 120 pM | 22.8 h |
| (a28) 9 | (b5) 13 | soluble | Biacore | 1.7 nM | 155.8 min |
| (a28) 9 | (b52) 15 | ImmTAC | Octet | 361 pM | 7.13 h |
| (a78I) 10 | (b52) 15 | ImmTAC | Octet | 210 pM | 7.6 h |
| (a78I) 10 | (b67) 20 | ImmTAC | Octet | 173 pM | 6.9 h |
| (a78I) 10 | (b68) 22 | ImmTAC | Octet | 334 pM | 4.7 h |
| (a78I) 10 | (b12) 14 | ImmTAC | Octet | 272 pM | 7.3 h |
| (a82I) 11 | (b65) 18 | ImmTAC | Biacore | 135 pM | 17.7 h |
| (a82I) 11 | (b52) 15 | ImmTAC | Biacore | 30.8 pM | 72 h |
| (a82I) 11 | (b67) 20 | ImmTAC | Octet | 226 pM | 8.5 h |
| (a82I) 11 | (b68) 22 | ImmTAC | Octet | 476 pM | 4.1 h |
| (a82I) 11 | (b12) 14 | ImmTAC | Octet | 547 pM | 5.3 h |
| (a82) 12 | (b52) 15 | ImmTAC[3] | Biacore | 40 pM | 64.2 h |
| (a82) 12 | (b65) 18 | ImmTAC[4] | Biacore | 166 pM | 18.7 h |
| (a86) 51 | (b71) 52 | ImmTAC | Biacore | 39.8 | 15.7 h | nd = not determined
[1]Corresponds to ImmTAC1 from Example 6, full alpha and beta chain sequences are provided in FIG. 5Corresponds to ImmTAC2 from Example 6, full alpha and beta chain sequences are provided in FIG. 6Corresponds to ImmTAC3 from Example 6, full alpha and beta chain sequences are provided in FIG. 7Corresponds to ImmTAC4 from Example 6, full alpha and beta chain sequences are provided in FIG. 8

These data demonstrate TCR alpha and beta chain sequences of the invention produce soluble TCRs and ImmTAC molecules with binding characteristics suitable for the development of immunotherapeutic reagents.

Example 6—Potent and Specific T Cell Redirection by ImmTAC Molecules of the Invention ImmTAC molecules containing alpha and beta variable chain sequences of the invention were tested for their ability to mediate potent and specific redirection of CD3+ T cells by ELISPOT assay, using interferon-γ (IFN-γ) secretion as a read out for T cell activation.

The sequences of the alpha and beta chains of the four ImmTAC molecules tested are provided in FIGS. 5-8.

Assays were performed using a human IFN-γ ELISPOT kit (BD Biosciences). Target cells were prepared at a density of 1×10$^6$/ml in assay medium (RPMI 1640 containing 10% heat inactivated FBS and 1% penicillin-streptomycin-L-glutamine) and plated at 50,000 cells per well in a volume of 50 μl. The following target cell lines were used in this example:

NCI-H1755 (NY-ESO-1$^{+ve}$; HLA-A*02$^{+ve}$) human lung cancer cell line (supplied by ATCC, cat. no: CRL-5892)
HAo5 (NY-ESO-1$^{-ve}$; HLA-A*02$^{+ve}$) human cardiac cells (supplied by Promocell, cat. no: C-12271)

Peripheral blood mononuclear cells (PBMC), isolated from fresh donor blood, were used as effector cells and plated at a concentration of 40,000 cells per well in a volume of 50 μl. Varying concentrations of ImmTAC were used, spanning the anticipated clinically relevant range, and added to the well in a volume of 50 μl.

Plates were prepared according to the manufacturer's instruction. Target cells, effector cells and ImmTAC molecules were added to the relevant wells and made up to a final volume of 200 μl with assay medium. All reactions were performed in triplicate. Control wells were also prepared with the omission of either ImmTAC, effector cells, or target cells. The plates were then incubated overnight (37° C./5% $CO_2$). The next day the plates were washed three times with wash buffer (1×PBS sachet, containing 0.05% P20, made up in deionised water). Primary detection antibody was then added to each well in a volume of 50 μl. Plates were incubated at room temperature for 2 hours prior to being washed again three times. Secondary detection was performed by adding 50 μl of diluted streptavidin-HRP to each well and incubating at room temperature for 1 hour and the washing step repeated. Plates were then washed twice with 200 μl PBS (pH 7.4). No more than 15 min prior to use, one drop (20 μl) of AEC chromogen was added to each 1 ml of AEC substrate and mixed and 50 μl added to each well. Spot development was monitored regularly and plates were washed in tap water to terminate the development reaction. The plates were then allowed to dry at room temperature for at least 2 hours prior to counting the spots using an CTL analyser with Immunospot software (Cellular Technology Limited).

The data presented in FIG. 9 show that ImmTAC molecules containing alpha and beta variable chain sequences of the invention are able to mediate potent T cell redirection against HLA-A*02$^{+ve}$ cancer cells expressing target antigen. No activity was observed against HLA-A*02$^{+ve}$ antigen negative cells. These data indicate that ImmTAC molecules are target cell specific within the clinically relevant concentration range (≤1 nM).

Figure 10:
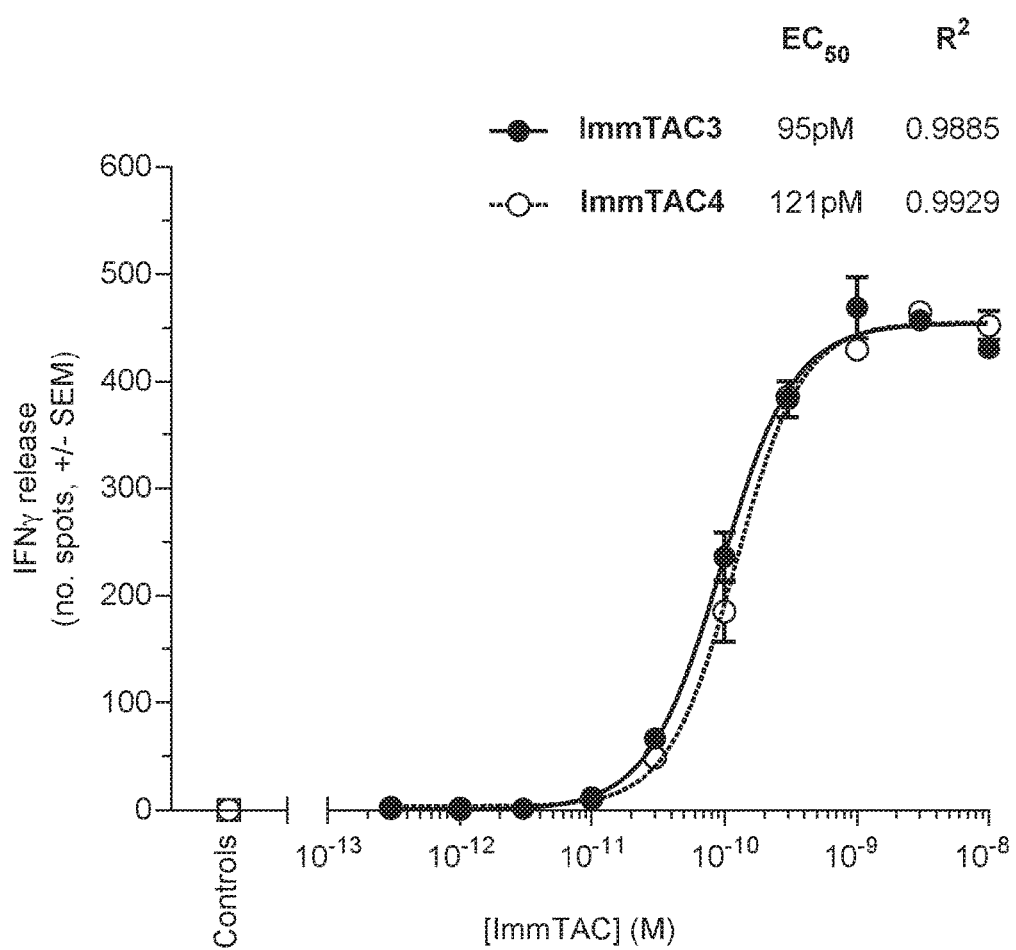
FIG. 10 shows further potency testing for 2 ImmTAC molecules of the invention.

Further assessment of potency was carried out for ImmTAC molecules 3 and 4 to determine EC50 values. ELISpot assays were performed as described above with ImmTAC concentrations ranging from 10$^{-13}$ M to 10$^{-8}$ M. Data were analysed using Prism 5.0 software (GraphPad) to calculate EC50 values. Values were determined as 95 μM and 121 μM for ImmTAC molecules 3 and 4 respectively (FIG. 10). These data confirm the ability of these ImmTAC molecules to mediate a potent redirected T cell response.

Example 7—Further Specificity Testing of ImmTAC Molecules of the Invention

Further specificity testing of ImmTAC molecules was carried out against a panel of normal cells. ImmTAC molecules 2-4 (FIGS. 6-8) are used in this example. Interferon-γ (IFN-γ) secretion was used as a read out for T cell activation.

Assays were performed using an IFN-γ DuoSet ELISA kit (R&D Systems, Cat No: DY285) and carried out as instructed by the manufacturer. Briefly, IFN-γ was diluted to 10,000 μg/ml and 2 fold dilutions made to produce a standard curve. Target cells were counted and plated at 10,000 cells per well in 10 ul in assay media. ImmTAC molecules were diluted to give final concentrations of 2 nM and 1 nM in 10 ul per well. A control sample without ImmTAC was also prepared. Effector PBMCs were thawed and plated at 10,000 cells/well in 10 ul. The plates were incubated for 48 h before being developed and read.

In this example, NCI-H1755 cells were used as an antigen positive control and HTC-116 cells were used as an antigen negative control. The cell panel included cardiomyocytes (CM12, CM5 and CM10), aortic endothelial cells (HAo5), airway epithelial cells (HCAEC2 and HCAEC5) skeletal muscle myoblasts (HSkMM3) and HPF9 cells. All cell lines were HLA-A*02$^{+ve}$. Assays were performed in triplicate.

Figure 11:
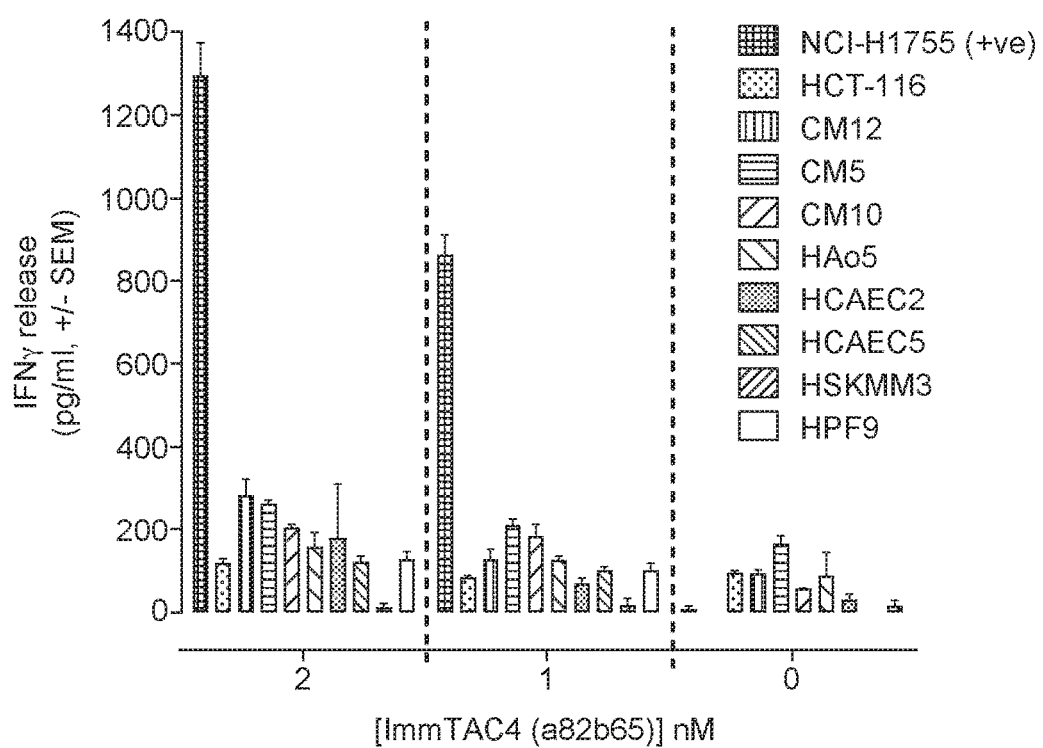
FIG. 11 shows further specificity testing for 3 ImmTAC molecules of the invention.

The data presented in FIG. 11 demonstrate minimal IFN-γ production in the presence of cell lines derived from normal tissues, relative to antigen positive cancer cell lines, within the therapeutically relevant ImmTAC concentration range. These data indicate that ImmTAC molecules of the invention have a high level of specificity and are therefore particularly suitable for therapeutic use.

Example 8—Potent Killing of Tumour Cells by ImmTAC Redirected T Cells

The ability of ImmTAC molecules of the invention to mediate potent redirected T cell killing of antigen positive tumour cells was investigated using the IncuCyte platform (Essen BioScience). This assay allows real time detection by microscopy of the release of Caspase-3/7, a marker for apoptosis.

Assays were performed using the CellPlayer 96-well Caspase-3/7 apoptosis assay kit (Essen BioScience, Cat. No. 4440) and carried out according the manufacturers protocol. Briefly, target cells (NCI-H1755—NYESO$^{+ve}$ HLA A*02$^{+ve}$ or HCT-116—NYESO$^{-ve}$ HLA A*02$^{+ve}$) were plated at 5000 cells per well and incubated overnight to allow them to adhere. ImmTAC solutions were prepared at concentrations between 2.16 nM and 8.8 μM. 25 ul of each concentration was added to the relevant well. PBMCs were used as effector cells and plated at 50,000 per well in 50 ul. A control sample without ImmTAC was also prepared. NucView assay reagent was made up at 30 uM and 25 ul added to every well (giving 5 uM final conc). The plate was placed in the IncuCyte instrument and images taken every 2 hours (1 image per well) over 3 days. The number of apoptotic cells in each image was determined and recorded as no. objects per mm$^2$. Assays were performed in triplicate.

Figure 12:
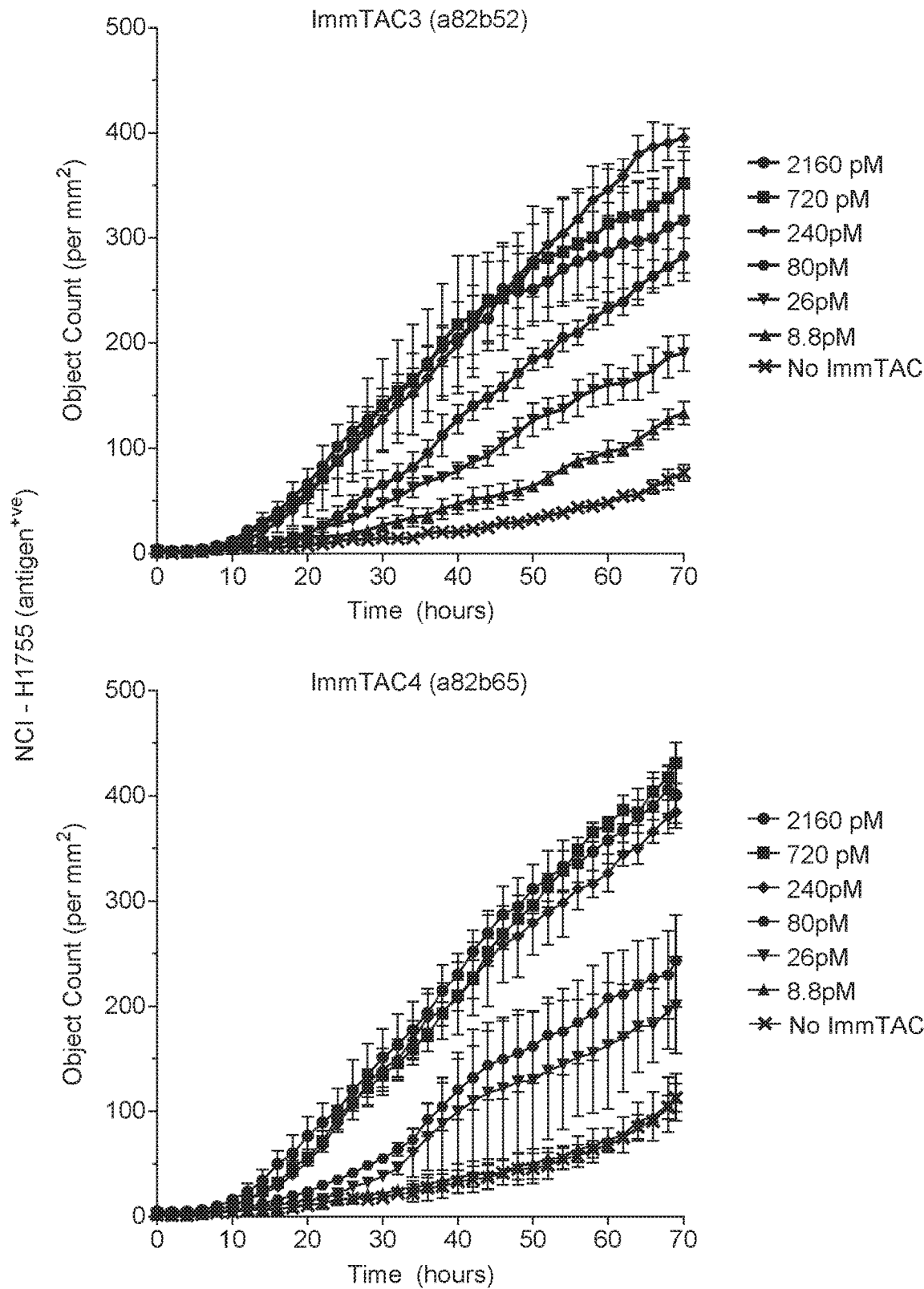
FIG. 12 shows tumour cell killing by ImmTAC redirected T cells.
Figure 12:
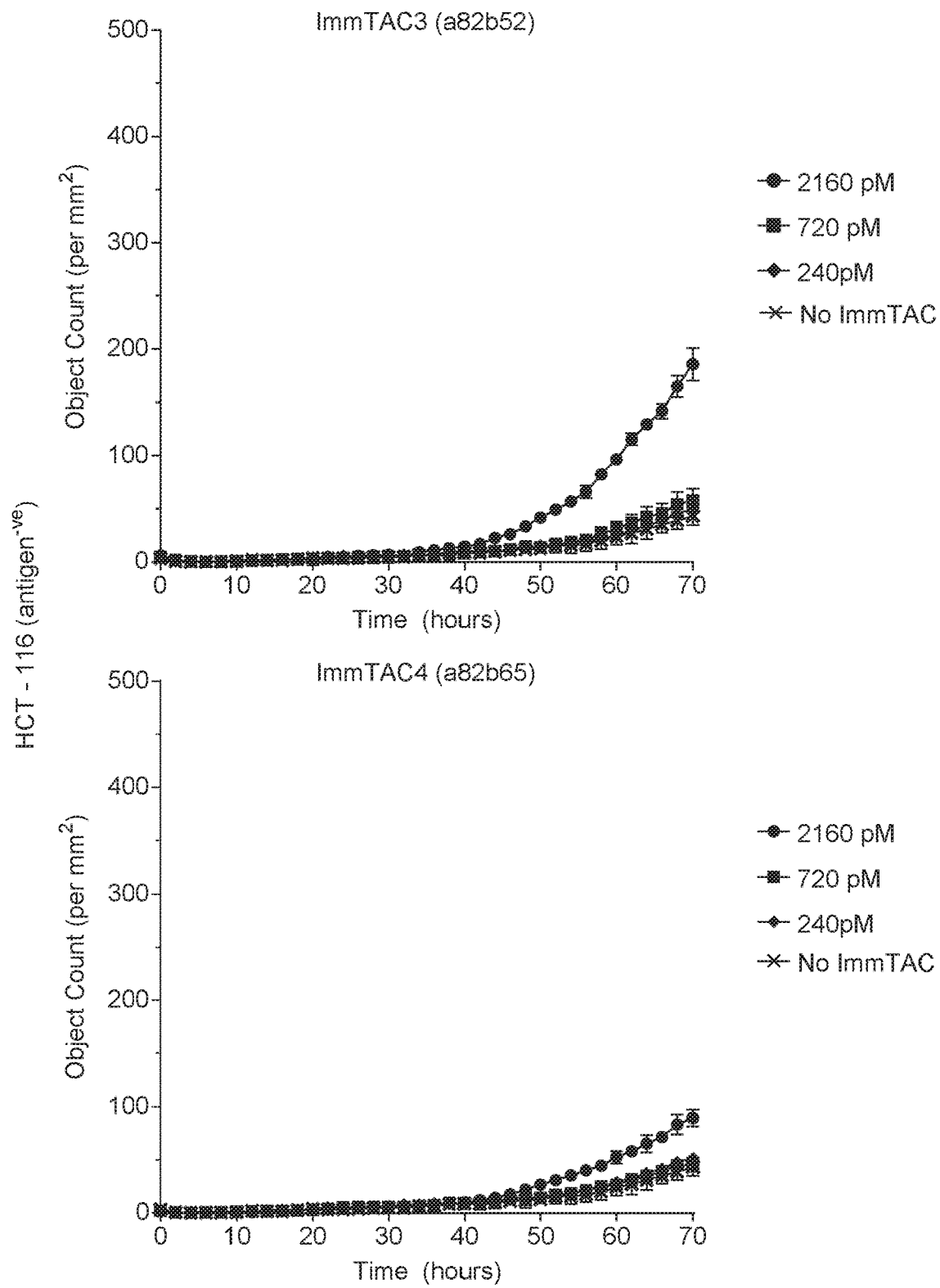

The data presented in FIG. 12 show real-time killing of tumour cells by ImmTAC redirected T cells. Results are presented for ImmTAC3 and ImmTAC4. Both ImmTAC molecules shows T cell redirected killing of antigen positive tumour cells at concentrations as low as 26 μM. ImmTAC3 shows T cell redirected killing below 10 μM. Low level killing of antigen negative cells is only observed at the highest concentration (2.16 nM).

These data confirm that ImmTAC3 and immTAC4 mediate potent redirected T cell killing of antigen positive tumour cells within the therapeutically relevant concentration range.

The invention claimed is:

1. A soluble T cell receptor (TCR) having the property of binding to SLLMWITQC (SEQ ID NO: 1) HLA-A*02 complex and comprising a TCR alpha chain variable domain and a TCR beta chain variable domain, wherein
the alpha chain variable domain comprises an amino acid sequence that has at least 90% identity to SEQ ID NO: 12, and
the beta chain variable domain comprises an amino acid sequence that has at least 90% identity to SEQ ID NO: 15, and
the alpha chain variable domain sequence of amino acids residues 27-32 (CDR1), 50-57 (CDR2) and 91-107 (CDR3) and the beta chain variable domain sequence of amino acid residues 27-31 (CDR1), 49-55 (CDR2) and 93-106 (CDR3) are selected from one of the following:
a) alpha chain variable domain CDR1, CDR2 and CDR3 sequences provided in SEQ ID NOs: 41, 54 and 43, respectively, and beta chain variable domain CDR1, CDR2 and CDR3 sequences provided in SEQ ID NOs: 59, 60 and 61, respectively;
b) alpha chain variable domain CDR1, CDR2 and CDR3 sequences provided in SEQ ID NOs: 41, 54 and 43, respectively, and beta chain variable domain CDR1, CDR2 and CDR3 sequences provided in SEQ ID NOs: 59, 63 and 46, respectively;
c) alpha chain variable domain CDR1, CDR2 and CDR3 sequences provided in SEQ ID NOs: 41, 54 and 57, respectively, and beta chain variable domain CDR1, CDR2 and CDR3 sequences provided in SEQ ID NOs: 59, 60 and 61, respectively; or
d) alpha chain variable domain CDR1, CDR2 and CDR3 sequences provided in SEQ ID NOs: 41, 54 and 57, respectively, and beta chain variable domain CDR1, CDR2 and CDR3 sequences provided in SEQ ID NOs: 59, 63 and 46, respectively.

2. The TCR of claim 1, wherein the alpha chain variable domain and the beta chain variable domain are selected from one of the following:
a) an alpha chain variable domain sequence provided in SEQ ID NO: 7 and a beta chain variable domain sequence provided in SEQ ID NO: 15;
b) an alpha chain variable domain sequence provided in SEQ ID NO: 7 and a beta chain variable domain sequence provided in SEQ ID NO: 18;
c) an alpha chain variable domain sequence provided in SEQ ID NO: 12 and a beta chain variable domain sequence provided in SEQ ID NO: 15; or
d) an alpha chain variable domain sequence provided in SEQ ID NO: 12 and a beta chain variable domain sequence provided in SEQ ID NO: 18.

3. The TCR of claim 1, which is an alpha-beta heterodimer, wherein the TCR further comprises an alpha chain TRAC constant domain sequence and a beta chain TRBC1 or TRBC2 constant domain sequence, wherein, optionally, the alpha and beta chain constant domain sequences are modified by truncation or substitution to delete the native disulfide bond between Cys4 of exon 2 of TRAC and Cys2 of exon 2 of TRBC1 or TRBC2, or, wherein, optionally, the alpha and/or beta chain constant domain sequence(s) are modified by substitution of cysteine residues for Thr 48 of TRAC and Ser 57 of TRBC1 or TRBC2, the said cysteines forming a non-native disulfide bond between the alpha and beta constant domains of the TCR.

4. The TCR of claim 1, which is in single chain format of the type Vα-L-Vβ, Vβ-L-Vα, Vα-Cα-L-Vβ, Vα-L-Vβ-Cβ, wherein Vα and Vβ are TCR α and β variable regions respectively, Cα and Cβ are TCR α and β constant regions respectively, and L is a linker sequence.

5. The TCR of claim 1, associated with a detectable label, a therapeutic agent or a pharmacokinetics modifying moiety.

6. A TCR anti-CD3 fusion comprising the TCR of claim 1, and an anti-CD3 antibody covalently linked to the C- or N-terminus of the alpha or beta chain of the TCR.

7. The TCR anti-CD3 fusion of claim 6, comprising an alpha chain variable domain selected from SEQ ID NO: 7 and 12 and comprising a beta chain variable domain selected from SEQ ID NO: 15 and 18, wherein, optionally the beta chain is linked to the anti-CD3 antibody sequence via a linker sequence, wherein, optionally, the linker sequence is selected from the group consisting of GGGGS (SEQ ID NO: 24), GGGSG (SEQ ID NO: 25), GGSGG (SEQ ID NO: 26), GSGGG (SEQ ID NO: 27), GSGGGP (SEQ ID NO: 28), GGEPS (SEQ ID NO: 29), GGEGGGP (SEQ ID NO: 30), and GGEGGGSEGGGS (SEQ ID NO: 31).

8. The TCR anti-CD3 fusion of claim 6, comprising an alpha chain variable domain consisting of an amino acid sequence of SEQ ID NO: 12 and a beta chain variable domain consisting of an amino acid sequence of SEQ ID NO: 15 and wherein the beta chain is linked to an anti-CD3 antibody via a linker sequence.

9. The TCR anti-CD3 fusion of claim 6, comprising an alpha chain variable domain consisting of an amino acid sequence of SEQ ID NO: 12 and a beta chain variable domain consisting of an amino acid sequence of SEQ ID NO: 15 and wherein the alpha chain is linked to an anti-CD3 antibody via a linker sequence.

10. A TCR anti-CD3 fusion according to claim 8, wherein the alpha chain variable domain consists of the amino acid sequence of SEQ ID NO: 12 and the beta chain variable domain consists of the amino acid sequence of SEQ ID NO: 15 and wherein the beta chain is linked to an anti-CD3 antibody via the linker sequence of SEQ ID NO: 24.

11. A pharmaceutical composition comprising the soluble TCR of claim 1, together with one or more pharmaceutically acceptable carriers or excipients.

12. The TCR of claim 1, wherein the TCR binds to the SLLMWITQC (SEQ ID NO: 1) HLA-A*02 complex with an affinity greater than 50 µM.

13. The TCR anti-CD3 fusion of claim 6, comprising an alpha chain consisting of SEQ ID NO: 37 and a beta chain consisting of SEQ ID NO: 38.

14. A TCR anti-CD3 fusion having the property of binding to SLLMWITQC (SEQ ID NO: 1) HLA-A*02 complex, wherein said TCR anti-CD3 fusion comprises an alpha chain amino acid sequence and a beta chain amino acid sequence pairing selected from the group consisting of:
  a) an alpha chain amino acid sequence at least 90% identical to SEQ ID NO: 32 and a beta chain amino acid sequence at least 90% identical to SEQ ID NO: 33;
  b) an alpha chain amino acid sequence at least 90% identical to SEQ ID NO: 35 and a beta chain amino acid sequence at least 90% identical to SEQ ID NO: 36;
  c) an alpha chain amino acid sequence at least 90% identical to SEQ ID NO: 37 and a beta chain amino acid sequence at least 90% identical to SEQ ID NO: 38; or
  d) an alpha chain amino acid sequence at least 90% identical to SEQ ID NO: 39 and a beta chain amino acid sequence at least 90% identical to SEQ ID NO: 40; and, wherein
the alpha chain variable domain sequence of amino acids residues 27-32 (CDR1), 50-57 (CDR2) and 91-107 (CDR3) and the beta chain variable domain sequence of amino acid residues 27-31 (CDR1), 49-55 (CDR2) and 93-106 (CDR3) are selected from one of the following:
 (i) alpha chain variable domain CDR1, CDR2 and CDR3 sequences provided in SEQ ID NOs: 41, 54 and 43, respectively, and beta chain variable domain CDR1, CDR2 and CDR3 sequences provided in SEQ ID NOs: 59, 60 and 61, respectively;
 (ii) alpha chain variable domain CDR1, CDR2 and CDR3 sequences provided in SEQ ID NOs: 41, 54 and 43, respectively, and beta chain variable domain CDR1, CDR2 and CDR3 sequences provided in SEQ ID NOs: 59, 63 and 46, respectively;
 (iii) alpha chain variable domain CDR1, CDR2 and CDR3 sequences provided in SEQ ID NOs: 41, 54 and 57, respectively, and beta chain variable domain CDR1, CDR2 and CDR3 sequences provided in SEQ ID NOs: 59, 60 and 61, respectively; or
 (iv) alpha chain variable domain CDR1, CDR2 and CDR3 sequences provided in SEQ ID NOs: 41, 54 and 57, respectively, and beta chain variable domain CDR1, CDR2 and CDR3 sequences provided in SEQ ID NOs: 59, 63 and 46, respectively.

* * * * *